(12) United States Patent
McCarthy et al.

(10) Patent No.: US 12,229,188 B2
(45) Date of Patent: Feb. 18, 2025

(54) MACHINE LEARNING TECHNIQUES FOR GENERATING DISEASE PREDICTION UTILIZING CROSS-TEMPORAL SEMI-STRUCTURED INPUT DATA

(71) Applicant: Optum Services (Ireland) Limited, Dublin (IE)

(72) Inventors: Michael J. McCarthy, Dublin (IE); Kieran O'Donoghue, Dublin (IE); Mostafa Bayomi, Dublin (IE); Neill Michael Byrne, Dublin (IE); Vijay S. Nori, Roswell, GA (US)

(73) Assignee: Optum Services (Ireland) Limited, Dublin (IE)

( * ) Notice: Subject to any disclaimer, the term of this patent is extended or adjusted under 35 U.S.C. 154(b) by 248 days.

(21) Appl. No.: 17/663,771

(22) Filed: May 17, 2022

(65) Prior Publication Data
US 2023/0376532 A1 Nov. 23, 2023

(51) Int. Cl.
*G06F 16/84* (2019.01)
*G06N 3/045* (2023.01)
*G06N 5/04* (2023.01)

(52) U.S. Cl.
CPC ............. *G06F 16/84* (2019.01); *G06N 3/045* (2023.01); *G06N 5/04* (2013.01)

(58) Field of Classification Search
CPC .......... G06F 16/84; G06N 3/045; G06N 5/04
See application file for complete search history.

(56) References Cited

U.S. PATENT DOCUMENTS

| | | |
|---|---|---|
| 6,788,965 B2 | 9/2004 | Ruchti et al. |
| 8,036,925 B2 | 10/2011 | Choubey |
| 8,321,251 B2 | 11/2012 | Opalach et al. |
| 8,751,266 B2 | 6/2014 | Stang |
| 9,147,041 B2 | 9/2015 | Amarasingham et al. |
| 9,324,119 B2 | 4/2016 | Singh et al. |
| 9,836,599 B2 | 12/2017 | Sheldon et al. |
| 10,231,622 B2 | 3/2019 | Soyao et al. |
| 10,249,389 B2 | 4/2019 | Athey et al. |

(Continued)

FOREIGN PATENT DOCUMENTS

| | | |
|---|---|---|
| CN | 112185569 A | 1/2021 |
| CN | 113241135 A | 8/2021 |

(Continued)

OTHER PUBLICATIONS

Non-Final Office Action for U.S. Appl. No. 17/469,005, dated Jan. 2, 2024, (46 pages), United States Patent and Trademark Office.

(Continued)

*Primary Examiner* — Pierre M Vital
*Assistant Examiner* — Jedidiah P Ferrer
(74) *Attorney, Agent, or Firm* — Alston & Bird LLP

(57) ABSTRACT

Various embodiments of the present invention provide methods, apparatus, systems, computing devices, computing entities, and/or the like for performing predictive data analysis using semi-structured input data. Certain embodiments of the present invention utilize systems, methods, and computer program products that perform predictive data analysis using semi-structured input data using at least one of techniques using inferred codified fields and temporally-arranged codified fields.

20 Claims, 11 Drawing Sheets

(56) References Cited

U.S. PATENT DOCUMENTS

| | | | |
|---|---|---|---|
| 10,404,526 | B2 | 9/2019 | Prabhakara et al. |
| 10,496,788 | B2 | 12/2019 | Amarasingham et al. |
| 10,579,928 | B2 | 3/2020 | Wang et al. |
| 10,692,589 | B2 | 6/2020 | Mueller-Wolf |
| 10,888,281 | B2 | 1/2021 | Shah et al. |
| 10,943,072 | B1* | 3/2021 | Jaganmohan .......... G06N 5/041 |
| 11,081,234 | B2 | 8/2021 | Pappada |
| 11,106,442 | B1* | 8/2021 | Hsiao .................... G06F 16/951 |
| 2005/0091084 | A1 | 4/2005 | McGuigan et al. |
| 2008/0214904 | A1 | 9/2008 | Saeed et al. |
| 2011/0071363 | A1 | 3/2011 | Montijo et al. |
| 2013/0035976 | A1 | 2/2013 | Buffett |
| 2013/0110576 | A1 | 5/2013 | Roy et al. |
| 2013/0172764 | A1 | 7/2013 | Buckley |
| 2013/0185097 | A1 | 7/2013 | Saria et al. |
| 2015/0213206 | A1 | 7/2015 | Amarasingham et al. |
| 2015/0286792 | A1 | 10/2015 | Gardner et al. |
| 2015/0289821 | A1 | 10/2015 | Rack-Gomer et al. |
| 2017/0061093 | A1 | 3/2017 | Amarasingham et al. |
| 2017/0111245 | A1 | 4/2017 | Ishakian et al. |
| 2017/0124269 | A1 | 5/2017 | McNair et al. |
| 2017/0357771 | A1 | 12/2017 | Connolly et al. |
| 2018/0211727 | A1 | 7/2018 | Zarkoob et al. |
| 2018/0225314 | A1* | 8/2018 | Devarao ............ G06F 16/2455 |
| 2018/0374580 | A1 | 12/2018 | Gupta et al. |
| 2019/0034590 | A1 | 1/2019 | Oren et al. |
| 2019/0034591 | A1 | 1/2019 | Mossin et al. |
| 2019/0036970 | A1 | 1/2019 | Shih et al. |
| 2019/0108912 | A1 | 4/2019 | Spurlock, III et al. |
| 2019/0147343 | A1 | 5/2019 | Lev et al. |
| 2019/0172587 | A1 | 6/2019 | Park et al. |
| 2019/0377818 | A1 | 12/2019 | Andritsos |
| 2020/0043612 | A1 | 2/2020 | McNair et al. |
| 2020/0074573 | A1 | 3/2020 | Op Den Buijs et al. |
| 2020/0160995 | A1 | 5/2020 | Kenig et al. |
| 2020/0185085 | A1 | 6/2020 | Mavrieudus et al. |
| 2020/0272919 | A1 | 8/2020 | Haimson et al. |
| 2020/0293527 | A1* | 9/2020 | Srivastav .............. G06F 16/285 |
| 2020/0356846 | A1* | 11/2020 | Saripalli ................ G06N 3/045 |
| 2020/0396231 | A1 | 12/2020 | Krebs et al. |
| 2020/0411176 | A1 | 12/2020 | Hadorn et al. |
| 2021/0082575 | A1 | 3/2021 | Ji et al. |
| 2021/0090733 | A1 | 3/2021 | Dibari et al. |
| 2021/0201184 | A1 | 7/2021 | Scheepens et al. |
| 2021/0241137 | A1 | 8/2021 | Jain et al. |
| 2021/0279644 | A1* | 9/2021 | Givental ................ G06N 3/044 |
| 2021/0286815 | A1* | 9/2021 | Aylett ................ G06F 16/24526 |
| 2021/0302953 | A1 | 9/2021 | Zhou et al. |
| 2021/0390668 | A1 | 12/2021 | Ren et al. |
| 2022/0291966 | A1 | 9/2022 | Masood et al. |
| 2022/0292339 | A1 | 9/2022 | Byrne et al. |
| 2022/0327404 | A1 | 10/2022 | Godden et al. |
| 2023/0024366 | A1 | 1/2023 | Krutka et al. |
| 2023/0075176 | A1 | 3/2023 | McCarthy et al. |
| 2023/0119186 | A1 | 4/2023 | O'Donoghue et al. |
| 2023/0122121 | A1 | 4/2023 | O'Donoghue et al. |
| 2023/0140828 | A1* | 5/2023 | Durvasula ................ G06N 5/04 705/7.37 |

FOREIGN PATENT DOCUMENTS

| | | |
|---|---|---|
| EP | 3767636 A1 | 1/2021 |
| WO | 2019/201997 A1 | 10/2019 |
| WO | 2021/115835 A1 | 6/2021 |

OTHER PUBLICATIONS

Marafino, Ben J. et al. "Predicting Preventable Hosptial Readmissions With Causal Machine Learning," Health Services Research, vol. 55, No. 6, Oct. 30, 2020, pp. 993-1002, DOI: 10.1111/1475-6773.13586, PMCID: PMC7704477, PMID: 33125706.

Wenke, Sam et al. "Contextual Recurrent Neural Networks," arXiv Preprint arXiv:1902.03455v1 [cs.LG] Feb. 9, 2019, (7 pages).

Assale, Michela et al. "The Revival of The Notes Field: Leveraging The Unstructured Content In Electronic Health Records," Frontiers In Medicine, vol. 6, Article 66, Apr. 17, 2019, pp. 1-23, DOI: 10.3389/fmed.2019.00066.

Bayramli, Ilkin et al. "Predictive Structured-Unstructured Interactions In EHR Models: A Case Study of Suicide Prediction," Nature Partner Journals|Digital Medicine, vol. 5, No. 15, Jan. 27, 2022, pp. 1-11, DOI: 10.1038/s41746-022-00558-0.

Camargo, Manuel et al. "Discovering Generative Models From Event Logs: Data-Driven Simulation vs Deep Learning," arXiv preprint arXiv:2009.03567v1 [cs.AI], Sep. 8, 2020, (12 pages).

Jacobi, Corinna et al. "Coming To Terms With Risk Factors For Eating Disorders—Application Of Risk Terminology and Suggestions For A General Taxonomy," Psychological Bulletin, vol. 130, No. 1, (2004), pp. 19-65, DOI: 10.1037/0033.2909.130.1.19.

Maslach, David et al. "Noise As Signal In Learning From Rare Events," Organization Science, vol. 29, No. 2, pp. 225-246, Apr. 2, 2018, DOI: 10.1287/orsc.2017.1179, ISSN: 1047-7039 (print), ISSN: 1526-5455 (online).

Miotto, Riccardo et al. "Deep Patient: An Unsupervised Representation To Predict The Future of Patients From The Electronic Health Records," Scientific Reports, vol. 6, No. 26094, May 17, 2016, pp. 1-10, DOI: 10.10.8/srep26094.

Mogren, Olof. "C-RNN-GAN: Continuous Recurrent Neural Networks With Adversarial Training," arXiv preprint arXiv:1611.09904 [cs.AI], Nov. 29, 2016, (6 pages).

Mukherjee, Ujal Kumar. "Managing The Risks and Potential of High-Tech Innovations-In-Use—Predictive Analytic Modeling With Big Data and A Longitudinal Field Study," A Dissertation Submitted to the Faculty of the Graduate School of the University of Minnesota, Jul. 2015, (165 pages).

Nolle, Timo et al. "DeepAlign: Alignment-Based Process Anomaly Correction Using Recurrent Neural Networks," In: Dustdar S., Yu E., Salinesi C., Rieu D., Pant V. (eds) Advanced Information Systems Engineering. CAISE 2020. Lecture Notes in Computer Science, vol. 12127, pp. 319-333, Springer, Cham. DOI: 10.1007/978-3-030-49435-3_20.

Syring, Anja F. et al. "Evaluating Conformance Measures In Process Mining Using Conformance Propositions," In book: Transactions on Petri Nets and Other Models of Concurrency XIV, Nov. 21, 2019, pp. 192-221, Springer, Berlin, Heidelberg. DOI: 10.1007/978-3-662-60651-3_8.

Tello-Leal Edgar et al. "Predicting Activities in Business with LSTM Recurrent Neural Networks," In 2018 ITU Kaleidoscope: Machine Learning for a 5G Future (ITU K), Nov. 26, 2018, (7 pages). IEEE. DOI: 10.23919/ITU-WT.2018.8598069.

Theis, Julian et al. "Adversarial System Variant Approximation To Quantify Process Model Generalization," IEEE Access, vol. 8, Oct. 23, 2020, pp. 194410-194427. DOI: 10.1109/ACCESS.2020. 3033450.

Xia, Bin et al. "LogGAN: A Log-Level Generative Adversarial Network For Anomaly Detection Using Permutation Event Modeling," Information Systems Frontiers, vol. 23, No. 2, Jun. 16, 2020, (14 pages). DOI: 10.1007/s10796-020-10026-3.

Zhang, Dongdong et al. "Combining Structured and Unstructured Data For Predictive Models: A Deep Learning Approach," BMC Medical Informatics and Decision Making, vol. 20, No. 280, Oct. 29, 2020, pp. 1-11, DOI: 10.1186/s12911-020-01297-6.

Darabi, Sajad et al. "TAPER: Time-Aware Patient EHR Representation," IEEE Journal of Biomedical and Health Informatics, vol. 24, Issue 11, pp. 3268-3275, Apr. 3, 2020 (ePub: Nov. 2020), DOI: 10.1109/JBHI.2020.2984931.

International Search Report and Written Opinion for International Application No. PCT/US2023/018975, dated Aug. 7, 2023, (15 pages), European Patent Office, Rijswijk, Netherlands.

Sarwar, Tabinda et al. "The Secondary Use Of Electronic Health Records For Data Mining: Data Characteristics and Challenges," ACM Computing Surveys, vol. 55, No. 2, Article 33, pp. 33:1-33:40, Jan. 18, 2022, DOI: 10.1145/3490234.

Choi et al., RETAIN: An Interpretable Predictive Model for Healthcare using Reverse Time Attention Mechanism, 2016, Advances in Neural Information Processing Systems, pp. 3512-3520 (Year: 2016).

(56) References Cited

OTHER PUBLICATIONS

Final Rejection Mailed on Aug. 23, 2024 for U.S. Appl. No. 17/469,005, 41 page(s).
Gao et al., Stage Net: Stage-Aware Neural Networks for Health Risk Prediction, 2020, WWW '20: Proceedings of The Web Conference 2020, pp. 530-540 (Year: 2020).
Hardt et al., Explaining an increase in predicted risk for clinical alerts, 2020, CHIL '20: Proceedings of the ACM Conference on Health, Inference, and Learning, pp. 80-89 (Year: 2020).
Non-Final Rejection Mailed on Aug. 27, 2024 for U.S. Appl. No. 17/196,543, 34 page(s).

* cited by examiner

402

Identify, based at least in part on the non-codified input data object, one or more data items associated with the non-codified input data object
601

Generate, based at least in part on the one or more data items associated with the non-codified input data object, an inferred record set comprising one or more inferred records
602

Generate the inferred codified field set based at least in part on each inferred record
603

FIG. 6

| member_id | srv_date | loinc | obs_value_string | source_dataset_id |
|---|---|---|---|---|
| | 2020-03-02 | 77147-7 | 77.0 | udw--20210325 |
| | 2020-06-21 | 2093-3 | 166.0 | udw--20210325 |
| | 2020-03-02 | 2075-0 | 103.0 | udw--20210325 |
| | 2020-03-02 | 17861-6 | 9.9 | udw--20210325 |
| | 2017-11-16 | 2075-0 | 103.0 | udw--20210325 |
| | 2019-06-17 | 6811-5 | 1007 | udw--20210325 |
| | 2019-06-17 | 48642-3 | 64.0 | udw--20210325 |
| | 2019-06-17 | 1920-8 | 13.0 | udw--20210325 |
| | 2019-06-17 | 1975-2 | 0.6 | udw--20210325 |
| | 2019-06-17 | 2823-3 | 4.4 | udw--20210325 |
| | 2017-01-31 | 14979-9 | 30.0 | udw--20210325 |
| | 2019-05-10 | 785-6 | 21.4 | udw--20210325 |
| | 2019-05-10 | 788-0 | 21.9 | udw--20210325 |
| | 2019-06-17 | 34643-9 | 0.6 | udw--20210325 |
| | 2017-02-23 | 777-3 | 849.0 | udw--20210325 |

```
┌─────────────────────────────────────────────┐
│ Identify a total value range associated with a source-
│ specific data type identifier associated with the respective
│ inferred record for the particular inferred codified field
│ 801
└─────────────────────────────────────────────┘
                      ↓
┌─────────────────────────────────────────────┐
│ Determine a plurality of value subranges for the total value
│ range
│ 802
└─────────────────────────────────────────────┘
                      ↓
┌─────────────────────────────────────────────┐
│ Determine a selected value subrange for the particular
│ inferred codified field based at least in part on the data
│ value field for the respective inferred record for the
│ particular inferred codified field
│ 803
└─────────────────────────────────────────────┘
                      ↓
┌─────────────────────────────────────────────┐
│ Generate the discretized data value code based at least in
│ part on the selected value subrange
│ 804
└─────────────────────────────────────────────┘
```

Visit 1: ['DX0_E785', 'LOINC_3094-0_(13.0,16.0)', 'PR_80053', 'PR_G8752', 'PR_96372', 'LOINC_2028-9_(27.0,+inf)', 'PR_G0439', 'DX0_Z1231', 'DX0_I700', 'LOINC_13457-7_(99.0,122.0)', 'LOINC_13458-5_(16.0,20.0)', 'DX0_R05', 'PR_G8732', 'LOINC_3097-3_(13.0,16.0)', 'PR_A0427', 'PR_G0463', 'PR_99232', 'PR_99223', 'LOINC_6768-6_(59.0,70.0)', 'LOINC_1920-8_(16.0,18.0)', 'LOINC_1975-2_(-inf,0.3)', 'PR_99214', 'DX0_Z720', 'DX0_B0229', 'PR_90674', 'DX0_Z0000', 'LOINC_1759-0_(1.9,+inf)', 'PR_G9899', 'PR_3023F', 'LOINC_2823-3_(4.3,4.5)']

Visit 2: ['DX0_G8929', 'DX0_F1920', 'DX0_E785', 'DX0_R918', 'DX0_E785', 'DX0_D72828', 'DX0_K5900', 'PR_80053', 'PR_G8752', 'DX0_F329', 'PR_1111F', 'DX0_J9611', 'DX0_R0603', 'PR_99232', 'DX0_J440', 'PR_G0463', 'DX0_D649', 'DX0_J206', 'DX0_J9621', 'PR_G9903', 'PR_G9899', 'PR_3023F', 'PR_G8482', 'DX0_F331']

Visit 3: ['DX0_R7309', 'PR_3017F', 'DX0_E785', 'POS_19', 'PR_G8541', 'DX0_Z87891', 'PR_92004', 'PR_G8752', 'DX0_F329', 'PR_G8753', 'DX0_R911', 'PR_1111F', 'DX0_110', 'DX0_J9611', 'PR_85027', 'PR_1036F', 'PR_94618', 'PR_G8732', 'PR_G9717', 'PR_G0463', 'DX0_D649', 'DX0_J9899', 'DX0_I471', 'PR_99214', 'PR_G8754', 'PR_99213', 'PR_G9903', 'DX0_J9621', 'PR_G9899', 'DX0_J449', 'PR_G8482', 'DX0_F331', 'POS_11', 'PR_G0297', 'PR_G8427', 'DX0_E119', 'DX0_F17200', 'PR_G8420', 'PR_71250']

Visit 4: ['DX0_G8929', 'RX_8831', 'LOINC_2161-8_(81.6,112.4)', 'LOINC_64131-6_(90.0,149.0)', 'DX0_Z7989', 'PR_80307', 'LOINC_61420-6_(2133.0,+inf)', 'RX_11582', 'PR_92083', 'PR_92136', 'RX_24024', 'LOINC_19055-3_(-inf,22.0)', 'RX_4763', 'DX0_H25013', 'LOINC_58363-3_(479.0,+inf)', 'RX_1617', 'PR_92020', 'PR_G0481', 'LOINC_58394-8_(304.0,589.0)', 'PR_99203', 'DX0_H2513', 'POS_11', 'DX0_F1120', 'DX0_M545', 'POS_81', 'LOINC_86224-3_(84.0,16068.0)', 'DX0_M5440', 'DX0_H401134', 'LOINC_58393-0_(2248.0,+inf)']

Patient ID: 5235346436
Disease Prediction Results:

| Disease | Predictive Output |
|---|---|
| Disease A | High risk |
| Disease B | Average risk |

FIG. 10

MACHINE LEARNING TECHNIQUES FOR GENERATING DISEASE PREDICTION UTILIZING CROSS-TEMPORAL SEMI-STRUCTURED INPUT DATA

BACKGROUND

Various embodiments of the present invention address technical challenges related to performing predictive data analysis utilizing a cross-temporal semi-structured input data and disclose innovative techniques for efficiently and effectively performing predictive data analysis using cross-temporal semi-structured input data.

BRIEF SUMMARY

In general, various embodiments of the present invention provide methods, apparatus, systems, computing devices, computing entities, and/or the like for performing predictive data analysis using cross-temporal semi-structured input data. Certain embodiments of the present invention utilize systems, methods, and computer program products that perform predictive data analysis using cross-temporal semi-structured input data by utilizing at least one of structured data, unstructured data, temporally-arranged codified field set, and temporally encoded prediction machine learning model.

In accordance with one aspect, a method is provided. In one embodiment, the method comprises: identifying a plurality of non-codified input data objects, wherein each non-codified input data object is generated by a respective data ingestion source of a plurality of data ingestion sources and is associated with a respective temporal marker of a plurality of temporal markers; for each non-codified input data object: generating, based at least in part on the non-codified input data object, an inferred record set comprising one or more inferred records, wherein: (i) each inferred record is associated with a record field set comprising a plurality of record fields, and (ii) the plurality of inferred record fields for a particular inferred record comprise an ingestion source identifier field, a source-specific data type identifier field, and a data value field, and generating, based at least in part on each inferred record, an inferred codified field set comprising a plurality of inferred codified fields, wherein: (i) each inferred codified field is associated with a respective inferred record and is generated based at least in part on the plurality of record fields for the respective inferred record, and (ii) each inferred codified field comprises an ingestion source identifier code that is generated based at least in part on the ingestion source identifier field for the respective inferred record, a source-specific data type identifier code that is generated based at least in part on the source-specific data type identifier field for the respective inferred record, and a discretized data value code that is generated based at least in part on the data value field for the respective inferred record; generating a temporally-arranged codified field set comprising a temporal arrangement of a group of input codified fields, wherein: (i) the group of input codified fields comprise each inferred codified field set and one or more input codified field sets, (ii) each input codified field is associated with a corresponding temporal marker, and (iii) the corresponding temporal marker for an inferred codified field is generated based at least in part on the respective temporal marker for the non-codified input data object that is used to generate the inferred codified field; generating, using a temporally encoded prediction machine learning model, and based at least in part on the temporally-arranged codified field set, a predictive output; and performing one or more prediction-based actions based at least in part on the temporally-arranged codified field set.

In accordance with another aspect, a computer program product is provided. The computer program product may comprise at least one computer-readable storage medium having computer-readable program code portions stored therein, the computer-readable program code portions comprising executable portions configured to: identify a plurality of non-codified input data objects, wherein each non-codified input data object is generated by a respective data ingestion source of a plurality of data ingestion sources and is associated with a respective temporal marker of a plurality of temporal markers; for each non-codified input data object: generate, based at least in part on the non-codified input data object, an inferred record set comprising one or more inferred records, wherein: (i) each inferred record is associated with a record field set comprising a plurality of record fields, and (ii) the plurality of inferred record fields for a particular inferred record comprise an ingestion source identifier field, a source-specific data type identifier field, and a data value field, and generate, based at least in part on each inferred record, an inferred codified field set comprising a plurality of inferred codified fields, wherein: (i) each inferred codified field is associated with a respective inferred record and is generated based at least in part on the plurality of record fields for the respective inferred record, and (ii) each inferred codified field comprises an ingestion source identifier code that is generated based at least in part on the ingestion source identifier field for the respective inferred record, a source-specific data type identifier code that is generated based at least in part on the source-specific data type identifier field for the respective inferred record, and a discretized data value code that is generated based at least in part on the data value field for the respective inferred record; generate a temporally-arranged codified field set comprising a temporal arrangement of a group of input codified fields, wherein: (i) the group of input codified fields comprise each inferred codified field set and one or more input codified field sets, (ii) each input codified field is associated with a corresponding temporal marker, and (iii) the corresponding temporal marker for an inferred codified field is generated based at least in part on the respective temporal marker for the non-codified input data object that is used to generate the inferred codified field; generate, using a temporally encoded prediction machine learning model, and based at least in part on the temporally-arranged codified field set, a predictive output; and perform one or more prediction-based actions based at least in part on the temporally-arranged codified field set.

In accordance with yet another aspect, an apparatus comprising at least one processor and at least one memory including computer program code is provided. In one embodiment, the at least one memory and the computer program code may be configured to, with the processor, cause the apparatus to: identify a plurality of non-codified input data objects, wherein each non-codified input data object is generated by a respective data ingestion source of a plurality of data ingestion sources and is associated with a respective temporal marker of a plurality of temporal markers; for each non-codified input data object: generate, based at least in part on the non-codified input data object, an inferred record set comprising one or more inferred records, wherein: (i) each inferred record is associated with a record field set comprising a plurality of record fields, and (ii) the plurality of inferred record fields for a particular inferred record comprise an ingestion source identifier field, a source-specific data type identifier field, and a data value field, and generate, based at least in part on each inferred record, an inferred codified field set comprising a plurality of inferred codified fields, wherein: (i) each inferred codified field is associated with a respective inferred record and is generated based at least in part on the plurality of record fields for the respective inferred record, and (ii) each inferred codified field comprises an ingestion source identifier code that is generated based at least in part on the ingestion source identifier field for the respective inferred record, a source-specific data type identifier code that is generated based at least in part on the source-specific data type identifier field for the respective inferred record, and a discretized data value code that is generated based at least in part on the data value field for the respective inferred record; generate a temporally-arranged codified field set comprising a temporal arrangement of a group of input codified fields, wherein: (i) the group of input codified fields comprise each inferred codified field set and one or more input codified field sets, (ii) each input codified field is associated with a corresponding temporal marker, and (iii) the corresponding temporal marker for an inferred codified field is generated based at least in part on the respective temporal marker for the non-codified input data object that is used to generate the inferred codified field; generate, using a temporally encoded prediction machine learning model, and based at least in part on the temporally-arranged codified field set, a predictive output; and perform one or more prediction-based actions based at least in part on the temporally-arranged codified field set.

BRIEF DESCRIPTION OF THE SEVERAL VIEWS OF THE DRAWINGS

Reference will now be made to the accompanying drawings, which are not necessarily drawn to scale, and wherein:

FIG. 6 provides a flowchart diagram of an example process for generating an inferred codified field for a particular non-codified input in accordance with some embodiments discussed herein.

FIGS. 7A-7B provide operational examples of table data objects in accordance with some embodiments discussed herein.

FIG. 8 provides a flowchart diagram of example process for generating discretized data value codes in accordance with some embodiments discussed herein.

FIG. 9 provides an operational example of a temporally-arranged codified field set in accordance with some embodiments discussed herein.

FIG. 10 provides an operational example of a prediction output user interface in accordance with some embodiments discussed herein.

DETAILED DESCRIPTION

Figure 1:
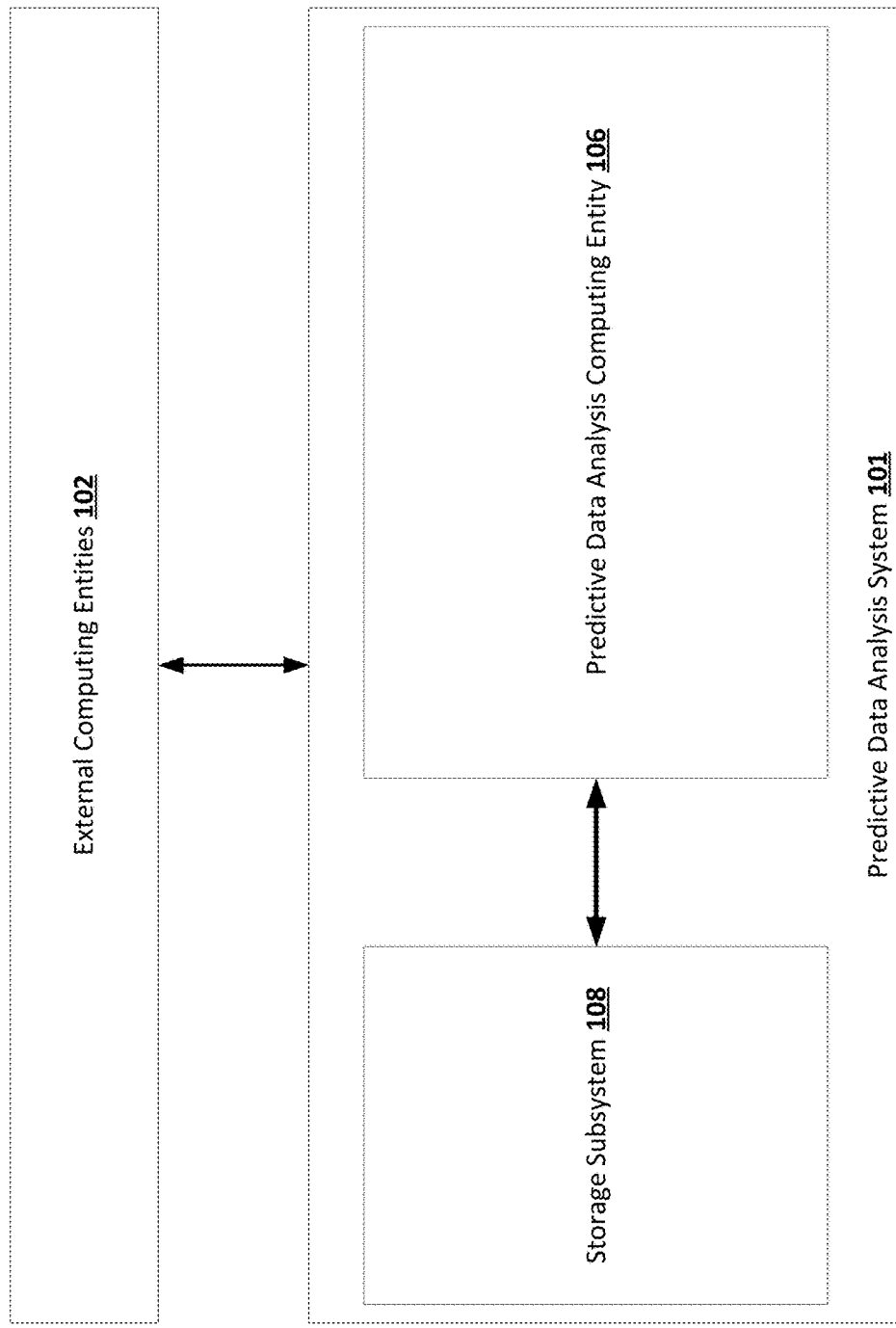
FIG. 1 provides an exemplary overview of an architecture that can be used to practice embodiments of the present invention.

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis with respect to disease prediction, one of ordinary skill in the art will recognize that the disclosed concepts can be used to perform other types of predictive data analysis.

I. OVERVIEW AND TECHNICAL ADVANTAGES

Various embodiments of the present invention improve computational efficiency of performing predictive machine learning operations on input data that comprises unstructured data and/or semi-structured data. Some existing machine learning frameworks performs complex and resource-intensive embedding operations on unstructured input data and/or semi-structured input data during a preprocessing stage before processing the resulting embeddings using final machine learning layers. In contrast, various embodiments of the present invention introduce computationally efficient techniques for converting unstructured input data and/or semi-structured input data into codified data, and in doing so avoid the need for performing complex and resource-intensive embedding operations on unstructured input data and/or semi-structured input data during a preprocessing stage before processing the resulting embeddings using final machine learning layers. Accordingly, by disclosing computationally efficient techniques for converting unstructured input data and/or semi-structured input data into codified data, various embodiments of the present invention improve computational efficiency of performing predictive machine learning operations on input data that comprises unstructured data and/or semi-structured data.

Various embodiments of the present invention address technical challenges related to efficiently and effectively performing predictive data analysis using cross-temporal semi-structured input data (e.g., structured and unstructured data). Various embodiments of the present invention disclose techniques for performing predictive data analysis steps/operations that are configured to encode unstructured data (e.g. convert unstructured data into codified data), techniques that are in turn configured to improve the efficiency of performing the noted predictive data analysis steps/operations and reliability of the generated results. Typically, predictive data analysis steps/operations are unable to incorporate related data (e.g., structured data and unstructured data) into a data collection scheme in an efficient manner and are inadequate for cross-correlating temporal data corresponding with different data types in a meaningful way. Additionally, existing techniques are time consuming and require a lot of computation resources. As a result, unstructured data that cannot be directly mapped to a temporal event record may be underutilized in performing predictive data analysis step/operations. There is a need for improved systems and methods configured to incorporate related data types in an efficient manner. Thus, various embodiments of the present invention improve predictive data analysis steps/operations by cross-correlating different temporal data types efficiently and effectively. Various embodiments of the present invention utilize predictive data analysis steps/operations (e.g., machine learning models, data ingestion, and/or the like) in order to determine an inferred codified field set for a non-codified input data object which can be utilized to map temporally related subset of unstructured data (e.g., unstructured event data) to structured data (e.g., structured event data) in a data collection scheme.

By facilitating efficient and reliable performance of predictive data analysis steps/operations through enabling inference of temporally mapped unstructured data and structured data, various embodiments of the present invention improve data retrieval efficiency, as well as data storage efficiency of various data storage systems. Furthermore, the techniques described herein enable faster and more accurate cross-correlation of disparate data types. This in turn increases the efficiency and reliability of data retrieval steps/operations and/or data query processing steps/operations across various data storage systems. Accordingly, by utilizing some or all of the innovative techniques disclosed herein for performing predictive data analysis steps/operations, various embodiments of the present invention increase efficiency and accuracy of data storage steps/operations, data retrieval steps/operations, and/or query processing steps/operations across various data storage systems, such as various data storage systems that are part of client-server data storage architectures. Via the noted advantages, various embodiments of the present invention make substantial technical contributions to the fields of predictive data analysis in particular and healthcare-related predictive data analysis in general. Moreover, various embodiments of the present invention make substantial contributions to the field of database systems and substantially improve state-of-the-art data storage systems.

Moreover, various embodiments of the present invention make important technical contributions to improving resource-usage efficiency of post-prediction systems by using temporally-arranged codified field sets to set the number of allowed computing entities used by the noted post-prediction systems. For example, in some embodiments, a predictive data analysis computing entity determines D inferred classifications for D prediction input data objects based at least in part on the D temporally-arranged codified field sets for the D prediction input data objects. Then, the count of prediction input data objects that are associated with an affirmative inferred classification, along with a resource utilization ratio for each prediction input data object, can be used to predict a predicted number of computing entities needed to perform post-prediction processing operations (e.g., automated investigation operations) with respect to the D prediction input data objects. For example, in some embodiments, the number of computing entities needed to perform post-prediction processing operations (e.g., automated investigation operations) with respect to D prediction input data objects can be determined based at least in part on the output of the equation: $R = \text{ceil}(\Sigma_k^{k=K} ur_k)$, where R is the predicted number of computing entities needed to perform post-prediction processing operations with respect to the D prediction input data object, ceil(·) is a ceiling function that returns the closest integer that is greater than or equal to the value provided as the input parameter of the ceiling function, k is an index variable that iterates over K prediction input data objects among the D temporally-arranged codified field sets that are associated with affirmative classifications, and $ur_k$ is the estimated resource utilization ratio for a kth prediction input data object that may be determined based at least in part on a count of utterances/tokens/words in the kth prediction input data object. In some embodiments, once R is generated, the predictive data analysis computing entity can use R to perform operational load balancing for a server system that is configured to perform post-prediction processing operations (e.g., automated investigation operations) with respect to D prediction input data objects. This may be done by allocating computing entities to the post-prediction processing operations if the number of currently-allocated computing entities is below R, and deallocating currently-allocated computing entities if the number of currently-allocated computing entities is above R.

An exemplary application of various embodiments of the present invention relates to performing predictive analysis to generate a disease prediction (e.g., disease risk profile) for an individual based at least in part on cross-temporal semi-structure input data that comprise structure data and unstructured data. A vast amount of medical data exists in various unstructured forms (e.g., medical charts incorporating hand-written notes, output streams from medical devices, search data from member applications (e.g., "myUHC,"), and notes from clinical tools (e.g., Pathway, Integrated Clinical User Experience, and Hawkeye). These unstructured data is not readily available for inclusion in code-based modeling frameworks. These unstructured data is not readily available for inclusion in code-based modeling frameworks. Incorporating any type of unstructured data in code-based modeling frameworks, at least in some embodiments, results in significant performance enhancement of these modeling frameworks, while also maintaining the critical clinical interpretability component of these models.

II. DEFINITIONS OF CERTAIN TERMS

The term "non-codified input data object" may refer to a data object that is configured to describe unstructured data, where, in some embodiments, unstructured data may refer to data that cannot be divided into semantically-defined data objects based at least in part on a predefined format of the data (e.g., free text data, hand-written note data, transcribed speech data, and/or the like). In some embodiments, a given non-codified input data object may be associated with a predictive entity (e.g., patient, healthcare plan member, and/or the like) with respect to which one more predictive data analysis operations are performed. In some embodiments, a given non-codified input data object may comprise unstructured patient data. Examples of unstructured patient data may include hand-written notes data of a medical provider as provided, for example, in a medical chart, data output streams from medical devices, data from various healthcare-related applications, notes from clinical tools, environmental data (e.g., PM2.5 levels, ozone, nitrogen dioxide, and/or other pollutants). A given non-codified input data object may be generated from a respective data ingestion source of a plurality of data ingestion sources. Furthermore the ingested data may be processed to generate an inferred codified field set based at least in part on inferred record set that is generated based at least in part on the non-codified input data object, where the inferred codified field set, may in turn be used to generate a temporally-arranged codified field set comprising each inferred codified field set and one or more input codified field sets, that may in turn be used to generate disease predictions and/or disease risk predictions, with respect to the predictive entity (e.g., patient).

The term "inferred record set" may refer to a data entity that is configured to describe one or more inferred records generated based at least in part on a non-codified input data object. In some embodiments, generating an inferred record set for a given non-codified input data object may comprise ingesting data items (e.g., attributes, features, observed data) associated with the non-codified input data object into a table data object of a plurality of table data objects, where a table data object may describe a data object comprising a plurality of rows and columns defining a plurality of record fields each configured for storing data. Each inferred record may be associated with a record field set comprising a plurality of record fields, where each record field set may correspond to a row in a corresponding table data object. In some embodiments, a record field set may comprise a member identifier field, an ingestion source identifier field, a source-specific data type identifier field, a data value field, and/or a temporal marker field. Accordingly, in various embodiments, a given inferred record may comprise a member identifier, an ingestion source identifier, a source-specific data type identifier, a data value, and/or a temporal marker that are each determined from the corresponding non-codified input data object. In some embodiments, each table data object of the plurality of table data objects may be associated with a particular ingestion source identifier of a plurality of ingestion source identifiers. For example, in some embodiments, a particular table data object may be configured to store data for non-codified input data objects determined from (or otherwise associated with) a respective data ingestion source having an ingestion source identifier of the particular table data object (e.g., having an ingestion source identifier associated with the particular table data object).

The term "inferred codified field set" may refer to a data object that describes encoded representations of a non-codified input data object (e.g., non-codified input data object that has been converted to codified data), where each inferred codified field of the inferred codified field set corresponds to an encoded (e.g., codified) representation of data (e.g., patient data) determined or otherwise extracted from the non-codified input data object. In some embodiments, an inferred codified field may comprise one or more encoded data items determined based at least in part from the non-codified input data object. Examples of data items that may be determined from a non-codified input data object include member identifier that describes a data object configured to uniquely identify the predictive entity with respect to which the non-codified input data object was generated, ingestion source identifier that describes a data entity configured to uniquely identify the data ingestion source that generated and/or incorporates the non-codified input data object, source-specific data type identifier that describes a data entity configured to uniquely identify a data type of observed data of interest in the non-codified input data object of a plurality of data types (e.g., diastolic blood pressure, systolic blood pressure, hydrocodone-creatine mass ration, and/or the like), data value that describes a data entity configured to describe a value of an observed data of interest, as determined from the non-codified input data object, a temporal marker (e.g., date), and/or the like.

An inferred codified field set may be generated using one or more of a variety of encoding techniques and/or models. In some embodiments, the encoding technique and/or encoding model for generating a particular inferred codified field set may be determined based at least in part on the ingestion source identifier for the data ingestion source associated with the particular inferred codified field set. For example, in some embodiments, an inferred codified field set for a given non-codified input data object may be generated utilizing a respective code generation model of a plurality of code generation models. In some embodiments, a code generation model may be a machine learning model. For example, in some embodiments, an inferred codified field set for a non-codified input data object that is a semantic/natural language non-codified input data object may be generated through some technique such as embedding, where an inferred record set of the non-codified input data object may be provided as input to the code generation machine learning model to generate the inferred codified field set.

The term "temporally-arranged codified field set" may refer to a data object configured to describe data (e.g., collection of codes/codified data) that may be used to perform predictive data analysis, such as disease prediction so as to, for example, predict the risk or likelihood of onset of a disease over time for a predictive entity. In some embodiments, a temporally-arranged codified field set comprises a group of input codified fields, where the group of input codified fields are associated with a plurality of events (e.g., a healthcare event, clinical visit, laboratory visit) with respect to the predictive entity. In some embodiments, the group of input codified fields comprise each inferred codified field set for the predictive entity, as determined from identified non-codified input data objects associated with the predictive entity, as well as one or more input codified field sets (described further below), where each inferred codified field set and each input codified field set is associated with an event (e.g., a healthcare event, clinical visit, laboratory visit) with respect to the predictive entity. Moreover, each event may be associated with a temporal marker, thus each inferred codified field set and each input codified field set may be associated with a temporal marker of a plurality of temporal markers, where a temporal marker may describe a day, month, and/or year of occurrence of a given event.

A temporally-arranged codified field set may be characterized by one or more temporal bins, where each temporal bin may be defined by a particular temporal marker of a plurality of temporal markers, and where each temporal bin may be sequentially arranged (e.g., positioned) within the temporally-arranged codified field set based at least in part on the temporal marker associated with the temporal bin. For example, given a first temporal bin and a second temporal bin, where the first temporal bin has a temporal marker (e.g., date) that is earlier than the temporal marker (e.g., date) for the second temporal bin, the first temporal bin may occur within the temporally-arranged codified field set before the second temporal bin. In some embodiments, the temporally-arranged codified field set may be configured such that temporal bins having later temporal markers occur first within the temporally-arranged codified field set. That is, in some embodiments, a temporally-arranged codified field set may describe a sequence of events (e.g., healthcare-related event) with respect to a patient, where each event is represented by codified unstructured patient data and/or structured claims-based data (e.g., healthcare-related codes) associated with the respective event. In some embodiments, each temporal bin comprises a respective codified field subset of a plurality of codified field subsets of the group of input codified fields, where each respective codified field subset comprises inferred codified fields and input codified fields having a temporal marker corresponding to the temporal marker of the respective temporal bin. For example, given T temporal markers that are associated with a temporal marker sequence, the temporally-arranged codified field set may comprise a subset sequence of T codified subsets, where the subset sequence is determined based at least in part on the temporal marker sequence.

The term "input codified field set" may refer to a data entity configured to describe structured data such as claims-based code that may be utilized to perform predictive data analysis, such as disease predictions with respect to the predictive entity associated with the input codified field set. For example, an input codified field set may comprise a plurality of codes from various healthcare claims (e.g., provider claims, pharmacy claims) with respect to a predictive entity, such as diagnosis codes (e.g., ICD-10), procedure codes (e.g., CPT, HCPCS), prescription codes (e.g., HICL), and/or place of service codes (e.g., CMS). In various embodiments, an input codified field set may be sequentially arranged within a temporally-arranged codified field set (as described above) along with inferred codified field sets of identified non-codified input data objects for the respective predictive entity based at least in part on the temporal marker associated with the input codified field set. In this manner, input codified field sets and inferred codified fields for the corresponding predictive input entity may be temporally cross-correlated to improve disease prediction with respect to the corresponding predictive entity.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SWIM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like, executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing predictive data analysis such as health related predictive data analysis. The architecture 100 includes a predictive data analysis system 101 configured to receive predictive data analysis requests from external computing entities 102, process the predictive data analysis requests to generate predictions, provide the generated predictions (e.g., health-related predictions) to the external computing entities 102, and automatically perform prediction-based actions based at least in part on the generated prediction.

An example of a prediction-based action that can be performed using the predictive data analysis system 101 is a request for generating a temporally-arranged codified field set corresponding to a patient based at least in part on cross-temporal semi-structured input data that describe a combination of structured data and unstructured data of the patient, in order to predict the risk and/or likelihood of one or more diseases with respect to the patient. A vast amount of medical data exists in various unstructured forms (e.g., medical charts incorporating handwritten notes, data output streams from medical devices, search data from member applications such as "myUHC" application—associated with UnitedHealth Group Inc., and notes from clinical tools such as Pathway, Integrated Clinical User Experience (ICUE), and Hawkeye—each associated with UnitedHealth Group Inc.). This unstructured data is not readily available for inclusion in code-based modeling frameworks. Incorporating any type of unstructured data (and/or semi-structured data) in code-based modeling frameworks, at least in some embodiments, results in significant performance enhancement of these modeling frameworks, while also maintaining the critical clinical interpretability component of these models.

In some embodiments, predictive data analysis system 101 may communicate with at least one of the external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software, and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more external computing entities 102, process the predictive data analysis requests to generate predictions corresponding to the predictive data analysis requests, provide the generated predictions to the external computing entities 102, and automatically perform prediction-based actions based at least in part on the generated predictions.

The storage subsystem 108 may be configured to store input data used by the predictive data analysis computing entity 106 to perform predictive data analysis (e.g., health-related predictions), as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

Figure 2:
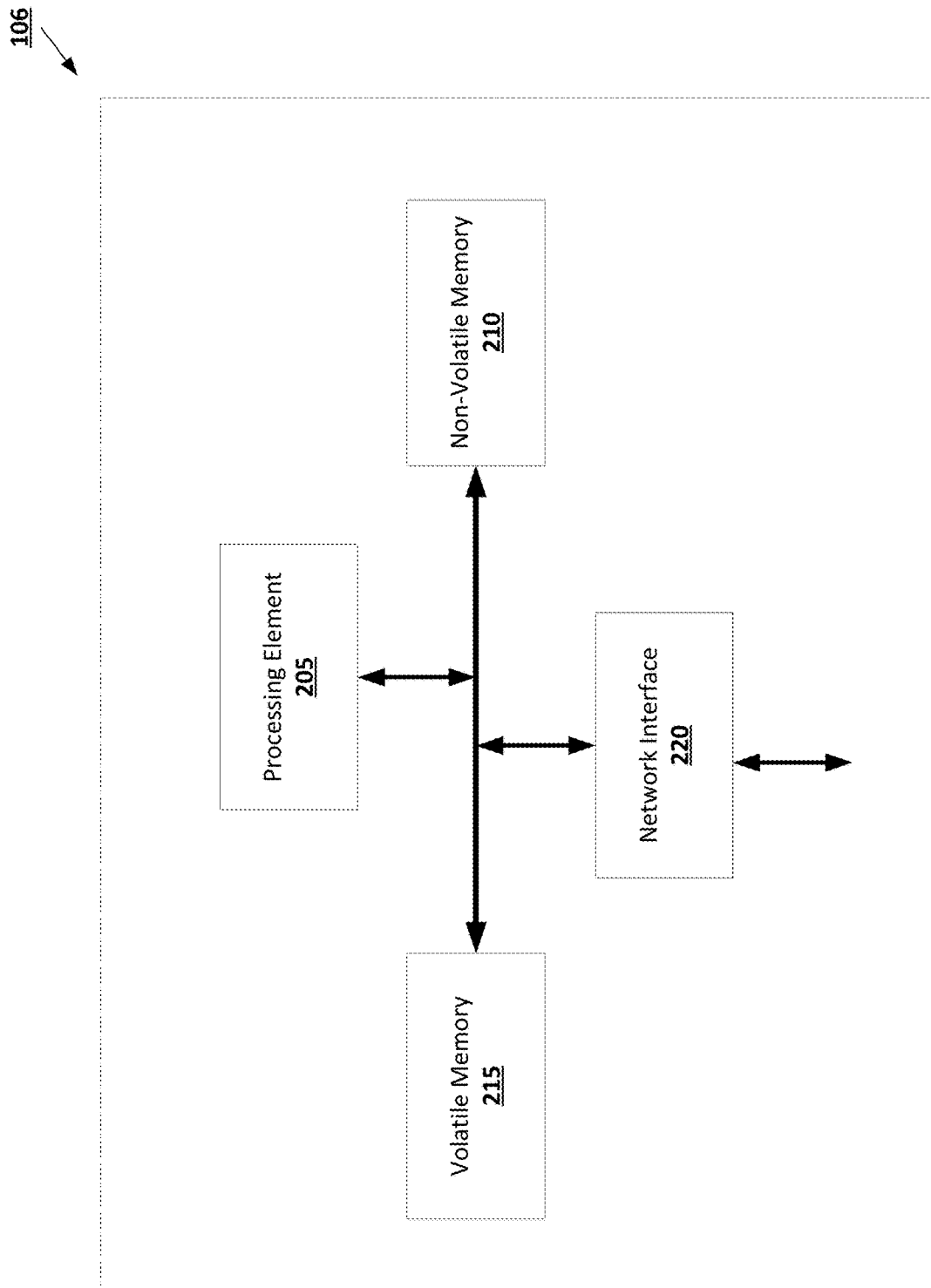
FIG. 2 provides an example predictive data analysis computing entity in accordance with some embodiments discussed herein.

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry, and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry, and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

Exemplary External Computing Entity

Figure 3:
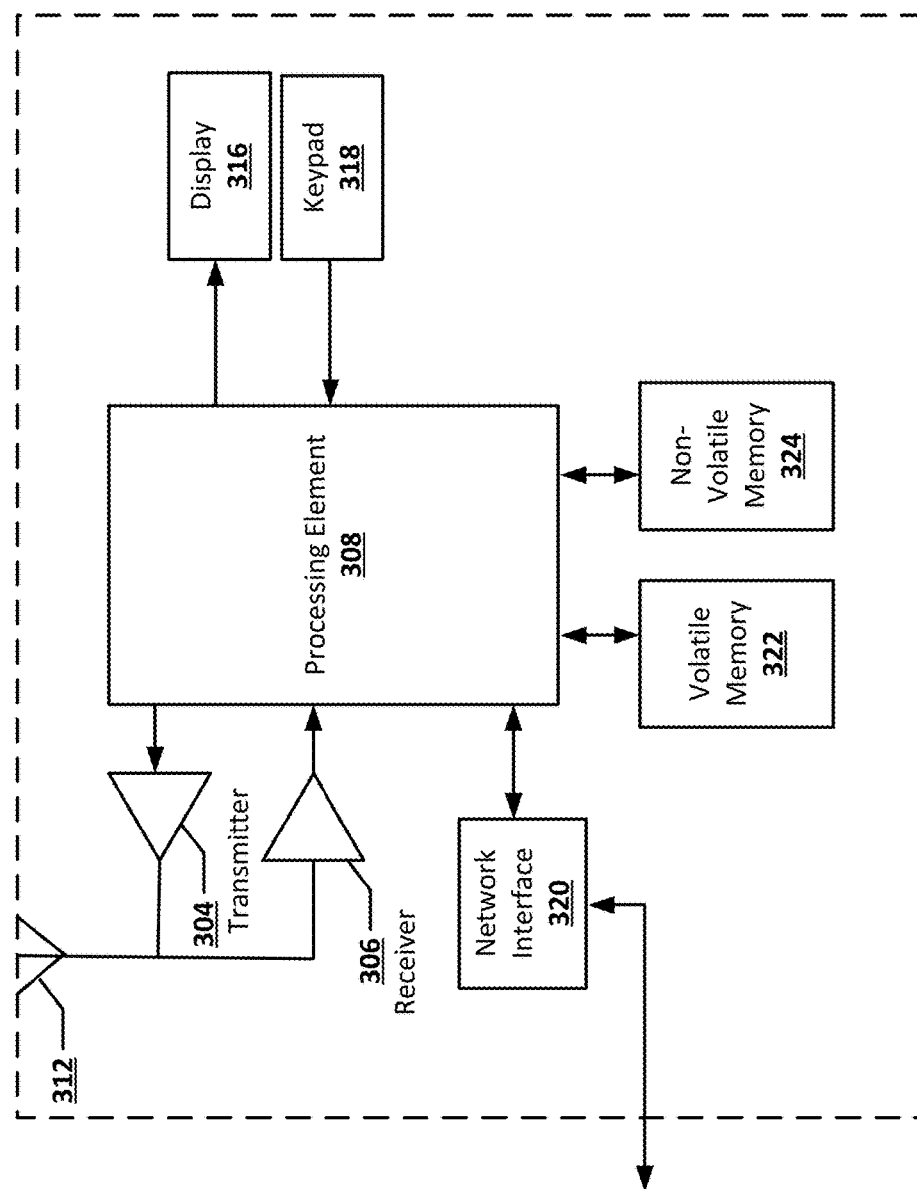
FIG. 3 provides an example external computing entity in accordance with some embodiments discussed herein.

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts, such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies, including RFID tags, indoor beacons or transmitters, Wi-Fi access points, cellular towers, nearby computing devices (e.g., smartphones, laptops), and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102, and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionalities that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

As described below, various embodiments of the present invention improve computational efficiency of performing predictive machine learning operations on input data that comprises unstructured data and/or semi-structured data. Some existing machine learning frameworks performs complex and resource-intensive embedding operations on unstructured input data and/or semi-structured input data during a preprocessing stage before processing the resulting embeddings using final machine learning layers. In contrast, various embodiments of the present invention introduce computationally efficient techniques for converting unstructured input data and/or semi-structured input data into codified data, and in doing so avoid the need for performing complex and resource-intensive embedding operations on unstructured input data and/or semi-structured input data during a preprocessing stage before processing the resulting embeddings using final machine learning layers. Accordingly, by disclosing computationally efficient techniques for converting unstructured input data and/or semi-structured input data into codified data, various embodiments of the present invention improve computational efficiency of performing predictive machine learning operations on input data that comprises unstructured data and/or semi-structured data.

Figure 4:
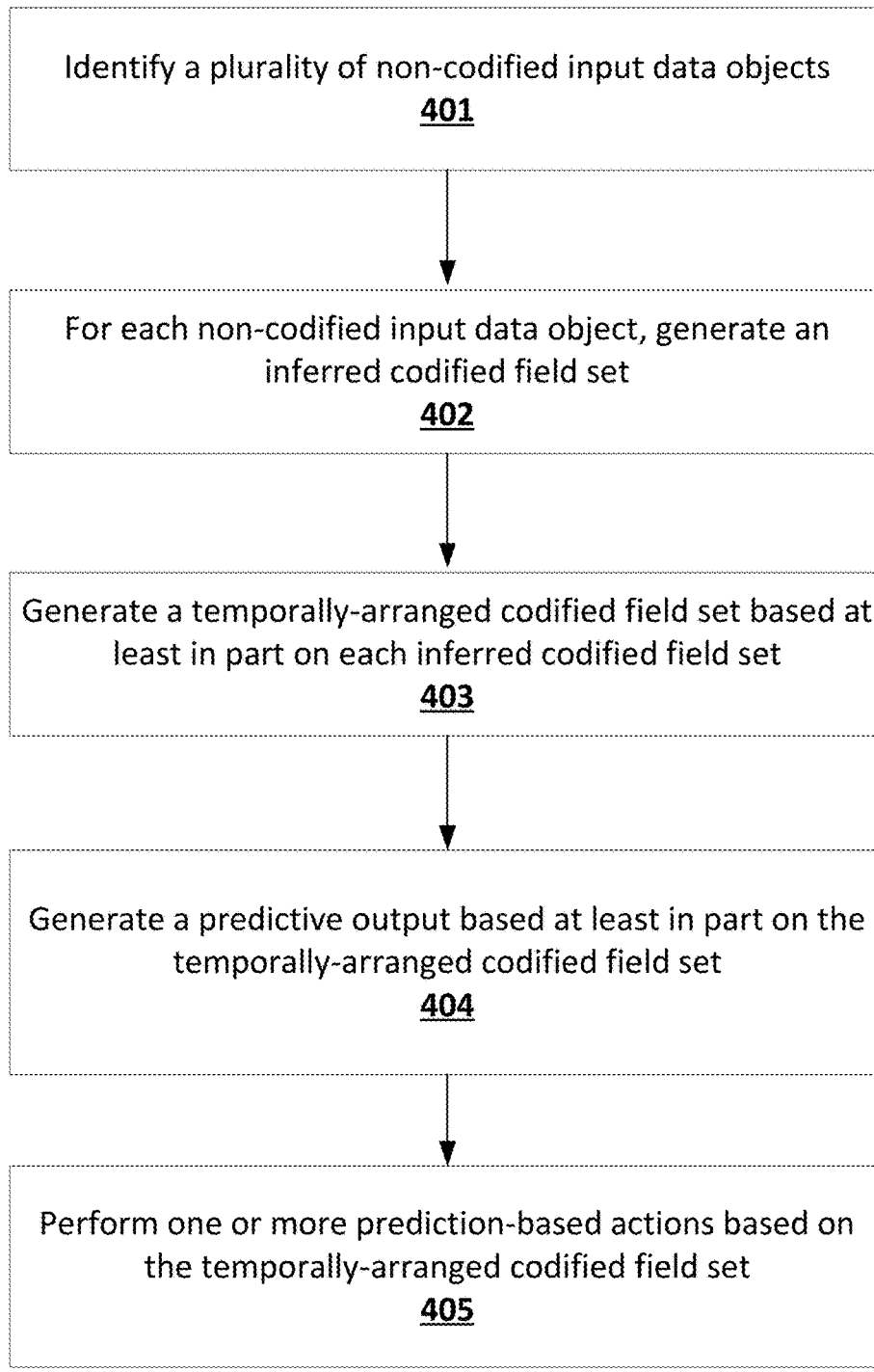
FIG. 4 is a flowchart diagram of an example process for generating a predictive output based at least in part on cross-temporal semi-structured input data in accordance with some embodiments discussed herein.

FIG. 4 provides a flowchart diagram of an example process for generating a predictive output based at least in part on cross-temporal semi-structured input data (e.g., unstructured input data and structured input data). The step/operation 401 begins when the predictive data analysis computing entity 106 identifies one or more non-codified input data objects associated with a predictive entity. For example, the predictive data analysis computing entity 106 may identify a plurality of non-codified input data objects associated with a particular predictive entity, where a predictive entity may describe an entity in relation to which one or more predictive tasks are performed. For example, the predictive entity may describe a particular individual (e.g., patient, healthcare plan member, and/or the like) with respect to whom one or more predictive tasks (e.g., predictive data analysis) are performed, so as to generate a disease prediction for the particular individual (e.g., likelihood of the particular individual developing one or more diseases).

A non-codified input data object may describe unstructured data, where, in some embodiments, unstructured data may refer to data that cannot be divided into semantically-defined data objects based at least in part on a predefined format of the data (e.g., free text data, hand-written note data, transcribed speech data, and/or the like). In some embodiments, a non-codified input data object may comprise unstructured patient data such as unstructured patient healthcare-related data. Examples of such unstructured healthcare-related data may include notes data (e.g., hand-written notes data, typed notes data), data output streams from medical devices, data from various applications (e.g., healthcare-related member applications such as myUHC—associated with UnitedHealth Group Inc.), data from clinical tools (e.g., Pathway, Integrated Clinical User Experience (ICUE), and/or Hawkeye—each associated with UnitedHealth Group, Inc.), and environmental data (e.g., PM2.5 levels, ozone, nitrogen dioxide, other pollutants, and/or the like). In some embodiments, unstructured data may encompass semi-structured data. Accordingly, in the noted embodiments, a non-codified input data object may comprise or otherwise describe unstructured data and semi-structured data.

A non-codified input data object may be generated from one of various data sources. In some embodiments, a given non-codified input data object may be generated by a data ingestion source or otherwise associated with a data ingestion source of a plurality of data ingestion sources, where a data ingestion source may describe a data source that is configured to generate at least in part unstructured data and/or comprise unstructured data. In some embodiments, each data ingestion source may be associated with an ingestion source identifier of a plurality of ingestion source identifiers.

A predictive entity may be associated with a plurality of non-codified input data objects, where each non-codified input data object may be generated by a data ingestion source or otherwise retrievable from a data ingestion source having a particular ingestion source identifier. As an example, medical charts (e.g., healthcare-related documents) generated by a healthcare provider may comprise notes (e.g., collection of data) detailing the healthcare provider's assessment, treatment, and/or other data in an unstructured data format (e.g., semantic/natural language), and may be associated with a semantic ingestion source identifier of one or more semantic ingestion source identifiers. As another example, laboratory data values (e.g., cholesterol levels, HbA1c, GFR, and/or the like) from laboratory tests may be presented and/or recorded in unstructured data format and may be associated with a laboratory ingestion source identifier of one or more laboratory ingestion source identifiers. As yet another example, data generated by a medical device may be presented and/or recorded in an unstructured data format (e.g., glucose levels from glucometers, electrocardiogram data from Holter monitors, and/or the like) and may be associated with a medical-device ingestion source identifier of one or more medical-device ingestion source identifiers. As a further example, data generated by one or more wearable devices may be presented and/or recorded in an unstructured data format (e.g., SpO2 levels from pulse oximeters, heart rate data from heart monitors, and/or the like) and may be associated with a wearable-device ingestion source identifier of one or more wearable-device ingestion source identifiers. As yet a further example, engagement data generated from one or more health-related applications, phone calls, (e.g., helpline calls), and/or the like may be presented and/or recorded in an unstructured data format and may be associated with an engagement ingestion source identifier of one or more engagement ingestion source identifiers. As yet another further example, behavioral data (e.g., knowledge, behavior attitude scores (KAB scores) compiled by a medical provider, nurse practitioner, clinician, and/or the like)) may be presented and/or recorded in an unstructured data format and may be associated with a behavioral ingestion source identifier of one or more behavioral ingestion source identifiers.

Figure 5:
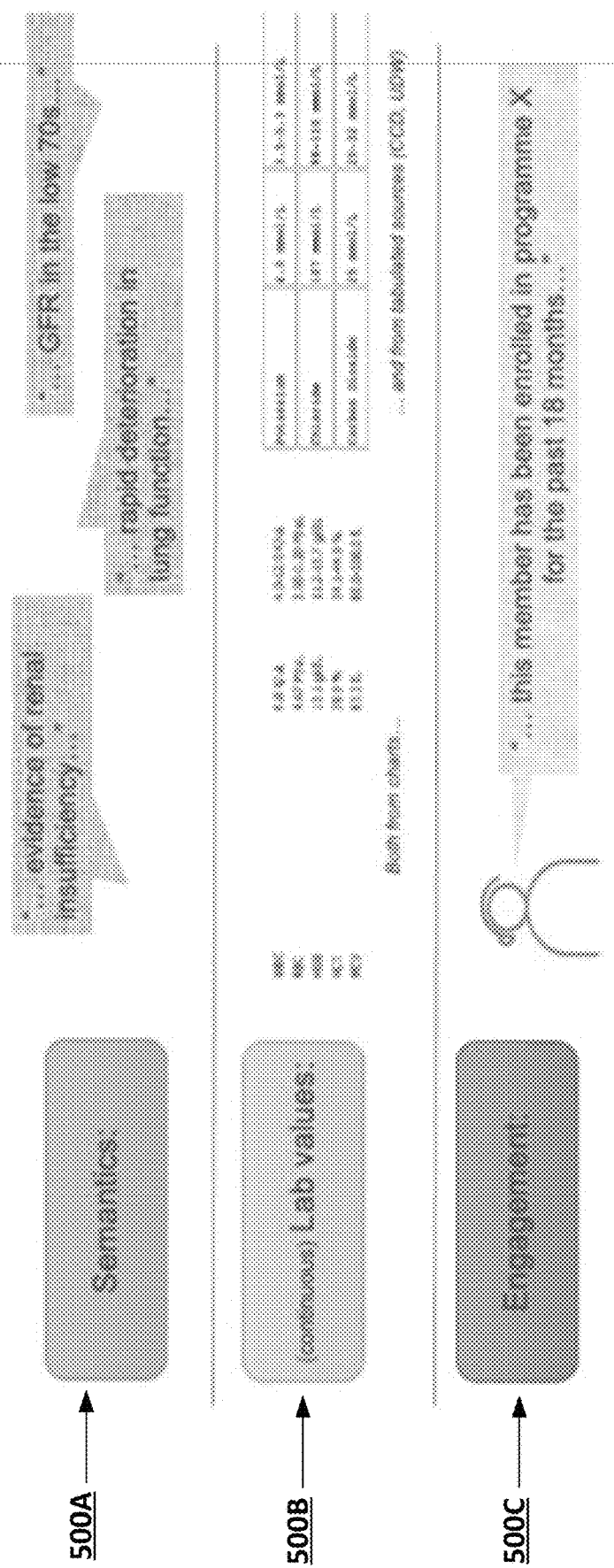
FIG. 5 provides an operational example of non-codified input data objects in accordance with some embodiments discussed herein.

FIG. 5 provides operational examples 500A-500C of example non-codified input data objects. As shown in FIG. 5, operational example 500A depicts unstructured semantic/natural language medical notes data as provided in a medical chart. As also shown in FIG. 5, operational example 500B depicts unstructured data values for laboratory tests as provided in a medical chart and/or tabulated sources. As further shown in FIG. 5, operational example 500C depicts unstructured natural language engagement data as provided in a document (e.g., phone call transcript).

In some embodiments, each non-codified input data object may be associated with an event (e.g., healthcare-related event, such as a patient hospital visit, emergency room visit, and/or the like). For example, each non-codified input data object may be generated based at least in part as a result of an event. For example, a non-codified input data object that is unstructured medical notes data may be generated when the predictive entity (e.g., patient) is attended to at (e.g., visits) a hospital. Thus, the non-codified input data object that is the unstructured medical notes data may be associated with the hospital visit (e.g. event). Moreover, in various embodiments, each event may be associated with a temporal marker, where a temporal marker may describe a day, month, and/or year associated with a particular event. Accordingly, in the noted example embodiments, each non-codified input data object may be associated with a temporal marker based at least in part on the event with respect to which the non-codified input data object was generated. For example, each non-codified input data object associated with the predictive entity may be associated with a respective temporal marker of a plurality of temporal markers. For example, given particular laboratory data obtained from laboratory tests performed on a patient, the temporal marker associated with the laboratory data may comprise the day, month, and/or year the laboratory tests was performed and/or the day, month, and/or year the sample for the test was collected. As another example, given particular medical notes data from a medical chart generated with respect to a healthcare-related visit (e.g., hospital visit, emergency room visit, laboratory visit, and/or the like) by a patient, the temporal marker associated with the medical notes data may comprise the day, month, and/or year the patient received services and/or was otherwise attended to by a healthcare provider. In some embodiments, the temporal marker may comprise a day of the week. In some embodiments, the temporal marker may comprise a month. In some embodiments, the temporal marker may be a year. In some embodiments, the temporal marker may comprise a day, a month, and a year.

In some embodiments, the predictive data analysis computing entity 106 may be configured to identify a plurality of non-codified input data objects associated with the predictive input entity, where each non-codified input data object of the plurality of non-codified input data objects may be generated by a respective data ingestion source of a plurality of data ingestion sources, and where each non-codified input data object may be associated with a respective temporal marker of a plurality of temporal markers.

Returning to FIG. 4, at step/operation 402, for each non-codified input data object, the predictive data analysis computing entity 106 generates an inferred codified field set comprising a plurality of inferred codified fields. An inferred codified field set may describe encoded representations of a non-codified input data field, where each inferred codified field of the inferred codified field set corresponds to an encoded representation of data determined or otherwise extracted from the non-codified input data object. In some embodiments, an inferred codified field may comprise one or more encoded data items determined based at least in part from the non-codified input data object. In some embodiments, examples of data items that may be determined from a non-codified input data object and encoded (e.g., codified) include member identifier that describes a data object configured to uniquely identify the predictive entity with respect to which the non-codified input data object was generated, ingestion source identifier that describes a data entity configured to uniquely identify the data ingestion source that generated and/or incorporates the non-codified input data object, source-specific data type identifier that describes a data entity configured to uniquely identify a data type of an observed data of interest in the non-codified input data object of a plurality of data types (e.g., diastolic blood pressure, systolic blood pressure, hydrocodone-creatine mass ratio, and/or the like), data value that describes a data entity configured to describe a value of an observed data of interest as determined from the non-codified input data object, a temporal marker (e.g., day, month, and/or year), and/or the like.

In some embodiments, for each non-codified input data object, each generated inferred codified field of the inferred codified field set may comprise an ingestion source identifier code (e.g., encoded ingestion source identifier), a source-specific data type identifier code (e.g., encoded source-specific data type identifier), and a discretized data value code. In some embodiments, an inferred codified field set for a non-codified input data object may be generated using one or more of a variety of encoding techniques and/or models. In some embodiments, the encoding technique and/or encoding model for generating a particular inferred codified field set may be determined based at least in part on the ingestion source identifier for the data ingestion source associated with the particular inferred codified field set. For example, in some embodiments, an inferred codified field set for a given non-codified input data object may be generated utilizing a respective code generation model of a plurality of code generation models. As noted above, in some embodiments, a code generation model may be a machine learning model. For example, in some embodiments, an inferred codified field set for a non-codified input data object that is a semantic/natural language non-codified input data object may be generated through some technique such as embedding, where an inferred record set (described further below) of the non-codified input data object may be provided as input to the code generation machine learning model to generate the inferred codified field set.

In some embodiments, the step/operation 402 may be performed in accordance with the example process 600 that is depicted in FIG. 6, which is an example process for generating an inferred codified field set for a particular non-codified input data object. In some embodiments, the example process 600 that is depicted in FIG. 6 begins at step/operation 601 when the predictive data analysis computing entity 106 identifies one or more data items associated with the particular non-codified input data object or otherwise described by the non-codified input data object (e.g., member identifier, ingestion source identifier, one or more source-specific data type identifiers, data values of one or more observed data of interest, and/or one or more temporal markers each corresponding to an observed data of interest).

At step/operation 602, the predictive data analysis computing entity 106 generates an inferred record set based at least in part on the one or more data items of the particular non-codified input data object (e.g., one or more data items associated with the particular non-codified input data object). In some embodiments, an inferred record set may comprise one or more inferred records, where each inferred record of the inferred record set may comprise one or more data items (e.g., member identifier, an ingestion source identifier, one or more source-specific data type identifiers, data values of one or more observed data of interest, and/or one or more temporal markers each corresponding to an observed data of interest) extracted or otherwise determined based at least in part from the particular non-codified input data object.

In some embodiments, generating an inferred record set for a non-codified input data object may comprise ingesting the non-codified input data object (e.g., data items of the non-codified input data object) into a table data object of one or more table data objects, where a table data object may describe a data object comprising a plurality of rows and columns defining a plurality of record fields each configured for storing data. In some embodiments, each row corresponds to record field set characterized by a group of record fields of the plurality of record fields. In some embodiments, each inferred record of the inferred record set of a non-codified input data object may be associated with a particular record field set (thus, a particular row in the corresponding table data object). In some embodiments, a record field set may comprise a member identifier field, an ingestion source identifier field, a source-specific data type identifier field, a data value field, and/or a temporal marker field. Accordingly, in some embodiments, a given inferred record may comprise a member identifier, an ingestion source identifier, a source-specific data type identifier, a data value, and/or a temporal marker that are each determined from the corresponding non-codified input data object.

For example, an inferred record set may comprise one or more inferred records, where each inferred record of the inferred record set may comprise one or more data items (e.g., member identifier, an ingestion source identifier, source-specific data type identifiers, data values of one or more observed data of interest, and/or one or more temporal markers each corresponding to an observed data of interest) that are stored in a respective record field of the record field set associated with the inferred record.

In some embodiments, each record field may be configured to store data having a particular data type corresponding to the record field. For example, in some embodiments, a given inferred record may be associated with a record field set comprising one or more record fields (e.g., plurality of record fields), where each record field is configured for storing a data item extracted from the non-codified input data object or otherwise determined based at least in part from the non-codified input data object, where each record field may be configured to store a particular data item having a particular data type (e.g., member identifier type, an ingestion source identifier type, source-specific data type identifier type, data value type, and/or temporal marker type). For example, in some embodiments, generating an inferred record set for a non-codified input data object may comprise ingesting data items identified or otherwise extracted from the non-codified input data object into a respective record field of the corresponding table data object based at least in part on the data type of each data item.

In some embodiments, the predictive data analysis computing entity 106 may be configured to generate each record field of a table data object utilizing one or more of a variety of techniques. For example, in some embodiments, generating the data value field for a particular inferred record that is associated with a particular non-codified input data object having a particular natural language field (e.g., associated with a semantic ingestion source identifier) may comprise generating a natural language embedding vector for the particular natural language field, and generating the data value field based at least in part on a vector distribution measure for the natural language embedding vector.

In various embodiments, each table data object may be associated with a particular data ingestion source of the plurality of data ingestion sources. For example, in various embodiments, each data ingestion source may be configured for storing data extracted or otherwise determined from a given non-codified input data object based at least in part on the ingestion source identifier for the ingestion source that generated the non-codified input data object and/or comprise the non-codified input data object.

One or more of a variety of techniques/models may be utilized to ingest a non-codified input data object into a respective table data object. In some embodiments, each non-codified input data object is associated with one or more techniques/models (e.g., ingestor models) for ingesting the non-codified input data object into the respective table data object. In some embodiments, the one or more techniques for ingesting a particular non-codified input data object into a respective table data object may be determined based at least in part on the ingestion source identifier associated with the particular non-codified input data object. For example, in some embodiments, the predictive data analysis computing entity 106 may be configured to ingest a non-codified input data object into the respective table data object utilizing an ingestor model that is selected based at least in part on the ingestion source identifier associated with the non-codified input data object.

In some embodiments, the ingestor models include semantic ingestor models configured for ingesting non-codified input data objects associated with semantic ingestion source identifiers, laboratory ingestor models configured for ingesting non-codified input data objects associated with laboratory ingestion source identifiers, engagement ingestor models configured for ingesting non-codified input data objects associated with engagement ingestion source identifiers, wearable-device ingestor models configured for ingesting non-codified input data objects associated with wearable-device ingestion source identifiers, medical-device ingestor models configured for ingesting non-codified input data objects associated with medical-device ingestion source identifiers, and behavioral ingestor models configured for ingesting non-codified data objects associated with behavioral ingestion source identifiers. Each ingestor model may utilize one or more ingesting techniques for ingesting a respective non-codified input data object. For example, in some embodiments, a non-codified input data object that is a semantic/natural language non-codified input data object (e.g., medical notes data from a medical chart) may be ingested into a respective table data object utilizing a frequency-inverse document frequency (TF-IDF) model. As another example, in some embodiments, a non-codified input data object that is a semantic/natural language non-codified input data object (e.g., medical notes from a medical chart) may be ingested into a respective table data object utilizing a bidirectional encoder representations from transformers (BERT) model.

Figure 7B:
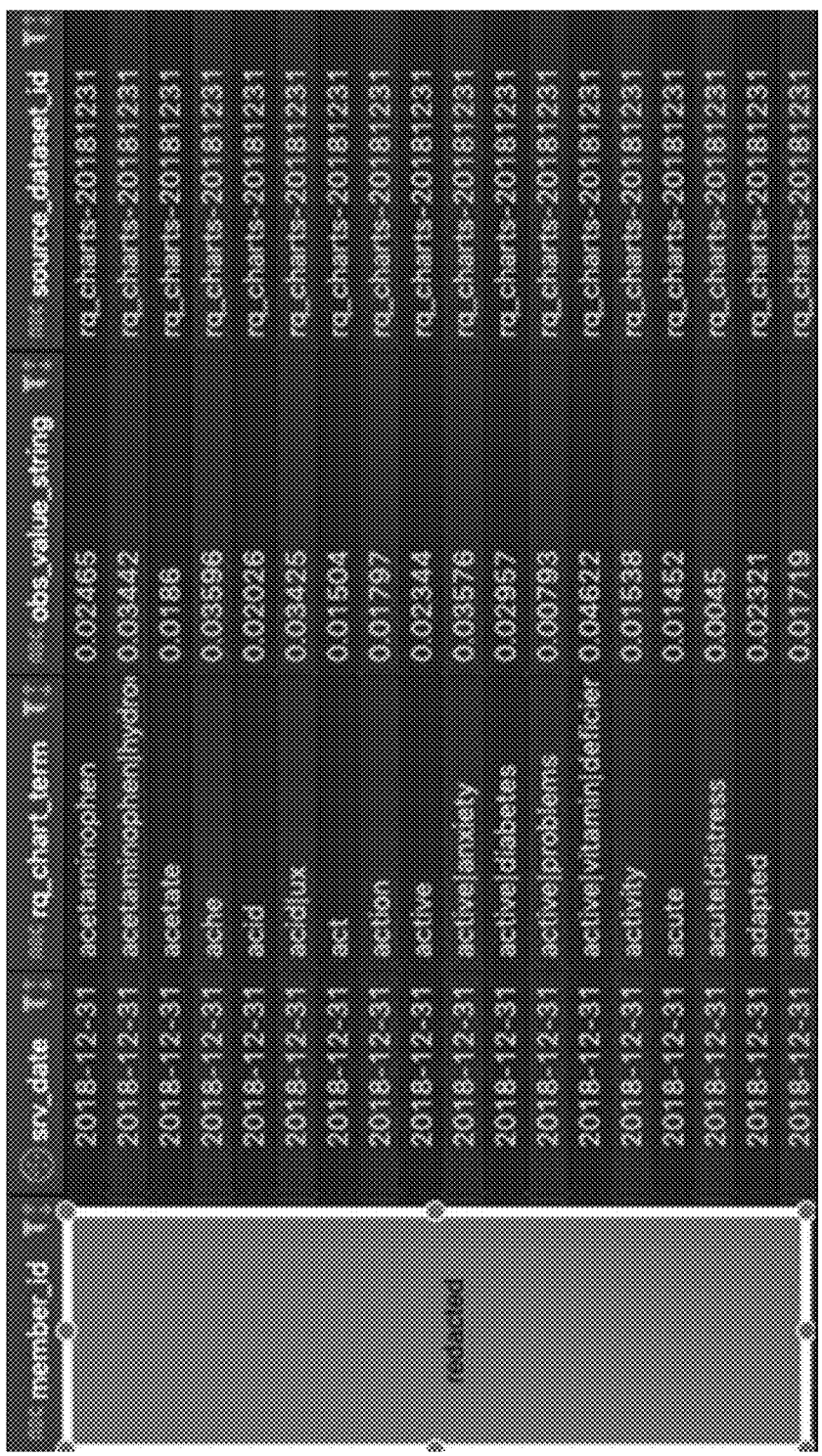

FIGS. 7A-7B provide operational examples 700A-700B of portions of example table data objects in accordance with some embodiments herein. FIG. 7A depicts a portion of a table data object that is associated with a laboratory ingestion source identifier. As depicted in FIG. 7A, the table data object comprises a plurality of record field sets each storing inferred records 702A-N, where each record field stores data associated with a particular data type 704A-704E with respect to the ingestion source identifier. Moreover, FIG. 7B depicts a portion of a table data object that is associated with a semantic ingestion source identifier. As depicted in FIG. 7B, the table data object comprises a plurality of record field sets each storing inferred records 712A-N, where each record field stores data associated with a particular data type 714A-E with respect to the ingestion source identifier.

Returning to FIG. 6 at step/operation 603, the predictive data analysis computing entity 106 generates, based at least in part on each inferred record, the inferred codified field set for the particular non-codified input data object. As discussed above, an inferred codified field set may be generated using one or more of a variety of encoding techniques and/or encoding models. In some embodiments, the encoding technique and/or encoding model for generating a particular inferred codified field set may be determined based at least in part on the ingestion source identifier for the data ingestion source associated with the particular inferred codified field set.

In some embodiments, the encoding models may include semantic encoding models configured for generating inferred codified fields for non-codified input data objects associated with a semantic ingestion source identifier. In some embodiments, the encoding models may include laboratory encoding models configured for generating inferred codified fields for non-codified input data objects associated with a laboratory ingestion source identifier. In some embodiments, the encoding models may include engagement encoding models configured for generating inferred codified fields for non-codified input data objects associated with an engagement ingestion source identifier. For example, the engagement ingestion model may be configured to generate inferred codified fields that describe whether or not an individual is enrolled in a healthcare-related program (e.g., chronic care management program). In some embodiments, the encoding models may include wearable-device encoding models configured for generating inferred codified fields for non-codified input data objects associated with a wearable-device ingestion source identifier. For example, the wearable-device encoding model may be configured to generate inferred codified fields based at least in part on a predefined measure with respect to a given data group (e.g., number of SpO2 measurement less than 80% within a defined timeframe).

In some embodiments, the encoding models may include medical-device encoding models configured for generating inferred codified fields for non-codified input data objects associated with a medical-device ingestion source identifier. For example, the medical-device encoding model may be configured to generate inferred codified fields based at least in part on the predefined measures with respect to a given data type, such as the corrected QT interval (QTc) on an electrocardiogram (ECG). In some embodiments, the encoding models may include behavioral encoding models configured for generating inferred codified fields for non-codified data objects associated with a behavioral ingestion source identifier. In some embodiments, one or more encoding models may be a machine learning model. For example, in some embodiments, an inferred codified field set for a non-codified input data object that is a semantic/natural language non-codified input data object may be generated through some technique such as embedding, where an inferred record set of the non-codified input data object may be provided as input to a code generation machine learning model to generate the inferred codified field set.

In various embodiments, the inferred codified field may be generated based at least in part on the plurality of record fields for the respective inferred record associated with the non-codified input data object (e.g., inferred record generated in step/operation 602). For example in various embodiments, generating an inferred codified field comprises generating one or more of an ingestion source identifier code (e.g., encoded ingestion source identifier), a source-specific data type identifier code (e.g., source-specific data type identifier), and/or a discretized data value code (e.g., encoded discretized data value of an observed data of interest). For example, in some embodiments, the predictive data analysis computing entity 106 may generate an ingestion source identifier code, a source-specific data type identifier code, and a discretized data value code. Additionally, in some embodiments, generating an inferred codified field may comprise concatenating the generated ingestion source identifier code, generated source-specific data type identifier code, and generated discretized data value code.

In some embodiments, the ingestion source identifier code for a given inferred codified field may be generated based at least in part on the ingestion source identifier field for the respective inferred record. In some embodiments, the source-specific data type identifier code may be generated based at least in part on the source-specific data type identifier field for the respective inferred record. In some embodiments, the discretized data value code may be generated based at least in part on the data value field for the respective inferred record. In some embodiments generating a discretized data value code may comprise discretizing continuous values into a plurality of discrete buckets (e.g., percentiles, quartiles, and/or the like).

In some embodiments, the discretized data value code for an inferred codified field may be generated in accordance with the example process that is depicted in FIG. 8, which is an example process for generating discretized data value codes. The process that is depicted in FIG. 8 begins at step/operation 801 when the predictive data analysis computing entity 106 identifies a total value range associated with a source-specific data type identifier associated with the respective inferred record for the particular inferred codified field, where a total value range may describe the possible range for the data type associated with the source-specific data type identifier. For example, the predictive data analysis computing entity 106 may identify that the total value range for a source-specific data type identifier for a systolic blood pressure data type is zero to three hundred and seventy mmHg (0-370 mmHg). As another example, the predictive data analysis computing entity 106 may identify that the total value range for a source-specific data type identifier for a diastolic blood pressure data type is zero to three hundred mmHg (0-300 mmHg).

At step/operation 802, the predictive data analysis computing entity 106 determines a plurality of value subranges for the total value range. For example, in some embodiments, the predictive data analysis computing entity 106 determines S value subranges for the total value range, where S may be defined by a range segmentation count hyperparameter for the source-specific data type identifier that is associated with the respective inferred record for the particular inferred codified field. For example, the predictive data analysis computing entity 106 may generate a plurality of bins each defining a disjoint range of the total value range. For example, given a diastolic blood pressure data type, the predictive data analysis computing entity 106 may determine value subranges that comprise "less than 80 mmHg," "80-120 mmHg," and "greater than 120 mmHg.) As another example, given a systolic blood pressure data type, the predictive data analysis computing entity 106 may determine value subranges that comprise "less than 120 mmHg," "120-140 mmHg," "141-180 mmHg," and "greater than 180 mmHg."

At step/operation 803, the predictive data analysis computing entity 106 determines a selected value subrange for the particular inferred codified field based at least in part on the data value field for the respective inferred record for the particular inferred codified field. For example, the predictive data analysis computing entity 106 may determine or otherwise select a corresponding value subrange based at least in part on the data value of the data value field for the respective inferred record for the particular inferred codified field. For example, consider that the data value in the respective data value field is a diastolic blood pressure of 125 mmHg. In the noted example, the predictive data analysis computing entity 106 may determine or otherwise select a value subrange of "greater than 120 mmHg."

At step/operation 804, the predictive data analysis computing entity 106 generates the discretized data value code based at least in part on the selected value subrange. In some embodiments, generating the discretized data value code based at least in part on the selected value subrange comprises identifying a subrange mapping scheme for the source-specific data type identifier, where the subrange mapping scheme maps each value subrange to a respective subrange coding symbol of a plurality of subrange coding symbols. Furthermore, in some embodiments, the predictive data analysis computing entity 106 then generates the discretized data value code based at least in part on the subrange mapping scheme. In some embodiments, generating the discretized data value code based at least in part on the subrange mapping scheme comprises identifying the respective subrange coding symbol for the selected value subrange based at least in part on the subrange mapping scheme, and generating the discretized data value code based at least in part on the respective subrange coding symbol. For example, in some embodiments, the subrange coding symbol of an example subrange mapping scheme for diastolic blood pressure that falls within the "greater than 120 mmHg" value subrange may be "(120.0, +inf)." As another example, the subrange coding symbol of an example subrange mapping scheme for diastolic blood pressure data value that falls within the "80-120 mmHg" value subrange may be (80.0, 120.0).

Returning to FIG. 4 at step/operation 403, the predictive data analysis computing entity 106 generates a temporally-arranged codified field set based at least in part on each inferred codified field set. A temporally-arranged codified field set may refer to a data object configured to describe a collection of sequentially ordered encoded data that may be used to perform predictive data analysis with respect to the predictive entity associated with the temporally-arranged codified field set. For example, in some embodiments, the temporally-arranged codified field set may be configured to be utilized to perform disease prediction with respect to the predictive entity, where the temporally-arranged codified field set comprises encoded representations (e.g., codes) of healthcare-related data of the predictive entity. In some embodiments, the temporally-arranged codified field set may comprise a data set characterized by a group of input codified fields comprising each inferred codified field set for the predictive entity and one or more input codified field sets for the predictive entity. An input codified field set may refer to a data entity configured to describe structured data such as claims-based code that may be utilized to perform predictive data analysis (e.g., disease predictions with respect to the predictive entity associated with the input codified field set). For example, an input codified field set may comprise a plurality of codes from various healthcare claims (e.g., provider claims, pharmacy claims) with respect to a predictive entity, such as diagnosis codes (e.g., ICD-10), procedure codes (e.g., CPT, HCPCS), prescription codes (e.g., HICL), and/or place of service codes (e.g., CMS). Accordingly, in some embodiments, the temporally-arranged codified field set may describe a sequential representation of codified unstructured data and structured claims-based code.

In some embodiments, the predictive data analysis computing entity 106 may configured to chronologically order/arrange each inferred codified field sets and each of the one or more input codified field sets of the group of input codified fields in order to generate the temporally-arranged codified field set. In some embodiments, as discussed above, each non-codified input data object may be associated with an event, where each event may be associated with a temporal marker. Thus, in the noted embodiments, each inferred codified field set may be associated with an event (e.g., a hospital visit, clinical visit, laboratory visit) with respect to the predictive entity, as well as a temporal marker. Additionally, in some embodiments, each input codified field set may be associated with an event (e.g., hospital event, clinical visit, laboratory visit) with respect to the predictive entity, where each event may be associated with a temporal marker (e.g., day, month, and/or year). In various embodiments, the predictive data analysis computing entity 106 may be configured to chronologically (e.g., sequentially) arrange the group of input codified fields based at least in part on the temporal marker associated with each inferred codified field set and input codified field sets.

In some embodiments, chronologically/sequentially arranging the group of input codified fields may comprise generating one or more temporal bins, such that the temporally-arranged codified field set is characterized by the one or more temporal bins, where each temporal bin may be defined by or otherwise associated with a particular temporal marker, and where each temporal bin may comprise a codified field subset of a plurality of codified field subsets of the group of input codified fields having a temporal marker that corresponds to the temporal marker of the respective temporal bin. In some embodiments, given T temporal markers that are associated with a temporal marker sequence, the temporally-arranged codified field set may comprise a subset sequence of T codified subsets, where the subset sequence is determined based at least in part on the temporal marker sequence. For example, given a first temporal bin and a second temporal bin, where the first temporal bin has a temporal marker (e.g., date) that is earlier than the temporal marker (e.g., date) for the second temporal bin, the first temporal bin may occur within the temporally-arranged codified field set before the second temporal bin. In some embodiments, the temporally-arranged codified field set may be configured such that temporal bins having later temporal markers occur first within the temporally-arranged codified field set. That is, in some embodiments, a temporally-arranged codified field set may describe a sequence of events (e.g., healthcare-related event) with respect to a predictive entity (e.g., patient, healthcare plan member, and/or the like), where each event is represented by codified unstructured patient data and/or structured claims-based data (e.g., claims-based code) associated with the respective event.

FIG. 9 provides an operational example 900 of a temporally-arranged codified field set. As shown in FIG. 9, the depicted temporally-arranged codified field comprises four temporal bins 902A-D comprising a group of input codified fields, where each temporal bin represents a healthcare-related visit defined by a temporal marker. Moreover, as shown in FIG. 9, each temporal bin comprises inferred codified field sets (e.g., 903, 904) and one or more input codified field sets (e.g., 905, 906).

At step/operation 404, the predictive data analysis computing entity 106 generates a predictive output based at least in part on the temporally-arranged codified field set. In various embodiments, the predictive data analysis computing entity 106 generates a predictive output that is configured to describe the risk of a disease for a predictive entity. In some embodiments, the predictive data analysis computing entity 106 generates a predictive output based at least in part on the temporally-arranged codified field set utilizing one or more techniques and/or one or more models. For example, in some embodiments, the predictive data analysis computing entity 106 generates the predictive output based at least in part on the temporally-arranged codified field by utilizing a temporally encoded prediction machine learning model. In some embodiments generating the predictive output may comprise training the temporally encoded prediction machine learning model to learn the sequence of the inferred codified fields and input codified fields of the temporally-arranged codified field, where, in some embodiments, as described above, each inferred codified field and input codified field may be associated with a healthcare-related visit by the predictive entity (e.g., patient). In some embodiments, the temporally encoded prediction machine learning model comprises a recurrent neural network machine learning model. In some embodiments, the temporally encoded prediction machine learning model comprises an encoder machine learning model that is trained as part of an encoder-decoder machine learning architecture. U.S. patent application Ser. No. 17/469,005 discloses example techniques that may be utilized in the present application for generating the predictive output.

At step/operation 405, the predictive data analysis computing entity 106 performs one or more prediction-based actions based at least in part on the temporally-arranged codified field set. For example, the predictive data analysis computing entity 106 may be configured to generate one or more physician alerts and/or one or more healthcare alerts based at least in part on the predictive output generated based at least in part on the temporally-arranged codified field set. As another example, the predictive data analysis computing entity 106 may be configured to generate one or more automated physician appointments, automated medical notes, automated prescription medications, automated physician instruction, and/or the like based at least in part on the predictive output generated based at least in part on the temporally-arranged codified field set. In some embodiments, the predictive data analysis computing entity 106 may be configured to generate user interface data for display using a display device of a computing entity (e.g., external computing entity 102). For example, in some embodiments, predictive data analysis computing entity 106 generates user interface data for one or more disease risks based at least in part on the temporally-arranged codified field set. In some embodiments, performing the prediction-based actions comprises generating user interface data for a prediction output user interface that displays the predictive output for a patient. An operational example of such a prediction output user interface 1000 is depicted in FIG. 10.

An example of a prediction-based actions that may be performed in accordance with various embodiments of the present invention relates to performing operational load balancing for post-prediction systems by using temporally-arranged codified field sets to set the number of allowed computing entities used by the noted post-prediction systems. For example, in some embodiments, a predictive data analysis computing entity determines D inferred classifications for D prediction input data objects based at least in part on the D temporally-arranged codified field sets for the D prediction input data objects. Then, the count of prediction input data objects that are associated with an affirmative inferred classification, along with a resource utilization ratio for each prediction input data object, can be used to predict a predicted number of computing entities needed to perform post-prediction processing operations (e.g., automated investigation operations) with respect to the D prediction input data objects. For example, in some embodiments, the number of computing entities needed to perform post-prediction processing operations (e.g., automated investigation operations) with respect to D prediction input data objects can be determined based at least in part on the output of the equation: $R=\text{ceil}(\Sigma_k^{k=K} ur_k)$, where R is the predicted number of computing entities needed to perform post-prediction processing operations with respect to the D prediction input data object, ceil(·) is a ceiling function that returns the closest integer that is greater than or equal to the value provided as the input parameter of the ceiling function, k is an index variable that iterates over K prediction input data objects among the D temporally-arranged codified field sets that are associated with affirmative classifications, and $ur_k$ is the estimated resource utilization ratio for a kth prediction input data object that may be determined based at least in part on a count of utterances/tokens/words in the kth prediction input data object. In some embodiments, once R is generated, the predictive data analysis computing entity can use R to perform operational load balancing for a server system that is configured to perform post-prediction processing operations (e.g., automated investigation operations) with respect to D prediction input data objects. This may be done by allocating computing entities to the post-prediction processing operations if the number of currently-allocated computing entities is below R, and deallocating currently-allocated computing entities if the number of currently-allocated computing entities is above R.

Accordingly, as described above, various embodiments of the present invention improve computational efficiency of performing predictive machine learning operations on input data that comprises unstructured data and/or semi-structured data. Some existing machine learning frameworks performs complex and resource-intensive embedding operations on unstructured input data and/or semi-structured input data during a preprocessing stage before processing the resulting embeddings using final machine learning layers. In contrast, various embodiments of the present invention introduce computationally efficient techniques for converting unstructured input data and/or semi-structured input data into codified data, and in doing so avoid the need for performing complex and resource-intensive embedding operations on unstructured input data and/or semi-structured input data during a preprocessing stage before processing the resulting embeddings using final machine learning layers. Accordingly, by disclosing computationally efficient techniques for converting unstructured input data and/or semi-structured input data into codified data, various embodiments of the present invention improve computational efficiency of performing predictive machine learning operations on input data that comprises unstructured data and/or semi-structured data.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
identifying, by one or more processors, a non-codified input data object that is generated by a respective data ingestion source of a plurality of data ingestion sources and is associated with a respective temporal marker of a plurality of temporal markers;
generating, by the one or more processors, an inferred record set comprising one or more inferred records based at least in part on the non-codified input data object, wherein: (i) an inferred record of the inferred record set is associated with a record field set comprising a plurality of record fields, and (ii) the plurality of record fields for the inferred record comprises an ingestion source identifier field, a source-specific data type identifier field, and a data value field;
generating, by the one or more processors, a discretized data value code for the inferred record based at least in part on (i) a subrange mapping scheme for a source-specific data type identifier code associated with the source-specific data type identifier field and (ii) the data value field for the inferred record;
generating, by the one or more processors, an inferred codified field set comprising a plurality of inferred codified fields based at least in part on the one or more inferred records, wherein: (i) an inferred codified field of the plurality of inferred codified fields is associated with the inferred record and is generated based at least in part on the plurality of record fields for the inferred record, and (ii) the inferred codified field comprises an ingestion source identifier code that is generated based at least in part on the ingestion source identifier field for the inferred record, a source-specific data type identifier code associated with the source-specific data type identifier field for the inferred record, and the discretized data value code;
generating, by the one or more processors, a temporally-arranged codified field set comprising a temporal arrangement of a group of input codified fields, wherein: (i) the group of input codified fields comprises the inferred codified field set and one or more input codified field sets, (ii) an input codified field of the one or more input codified field sets is associated with a corresponding temporal marker, and (iii) the corresponding temporal marker for the inferred codified field is generated based at least in part on the respective temporal marker for the non-codified input data object that is used to generate the inferred codified field;
generating, by the one or more processors and using a temporally encoded prediction machine learning model, a predictive output based at least in part on the temporally-arranged codified field set; and
performing, by the one or more processors, one or more prediction-based actions based at least in part on the temporally-arranged codified field set.

2. The computer-implemented method of claim 1, wherein, given T temporal markers that are associated with a temporal marker sequence:
the temporally-arranged codified field set comprises a subset sequence of T codified field subsets;
a codified field subset of the temporally-arranged codified field set is associated with an associated temporal marker in the temporal marker sequence; and
the subset sequence is determined based at least in part on the temporal marker sequence.

3. The computer-implemented method of claim 1, wherein generating the discretized data value code for the particular inferred codified field comprises:
identifying a total value range associated with the source-specific data type identifier code that is associated with the inferred record for the inferred codified field;
determining S value subranges for the total value range, wherein S is defined by a range segmentation count hyperparameter for the source-specific data type identifier code that is associated with the inferred record for the inferred codified field;
determining a selected value subrange from the S value subranges for the inferred codified field based at least in part on the data value field for the inferred record for the particular inferred codified field; and
generating the discretized data value code based at least in part on the selected value subrange.

4. The computer-implemented method of claim 3, wherein the subrange mapping scheme maps each value subrange in the S value subranges to a respective subrange coding symbol.

5. The computer-implemented method of claim 4, further comprising:
identifying the respective subrange coding symbol for the selected value subrange based at least in part on the subrange mapping scheme; and
generating the discretized data value code based at least in part on the respective subrange coding symbol.

6. The computer-implemented method of claim 1, wherein the temporally encoded prediction machine learning model comprises a recurrent neural network machine learning model.

7. The computer-implemented method of claim 1, wherein the temporally encoded prediction machine learning model comprises an encoder machine learning model that is trained as part of an encoder-decoder machine learning architecture.

8. The computer-implemented method of claim 1, further comprising:
generating a natural language embedding vector for a natural language field associated with the inferred record; and
generating the data value field based at least in part on a vector distribution measure for the natural language embedding vector.

9. A system comprising memory and one or more processors communicatively coupled to the memory, the one or more processors configured to:
identify a non-codified input data object that is generated by a respective data ingestion source of a plurality of data ingestion sources and is associated with a respective temporal marker of a plurality of temporal markers;
generate an inferred record set comprising one or more inferred records based at least in part on the non-codified input data object, wherein: (i) an inferred record of the inferred record set is associated with a record field set comprising a plurality of record fields, and (ii) the plurality of record fields for the inferred record comprises an ingestion source identifier field, a source-specific data type identifier field, and a data value field;
generate a discretized data value code for the inferred record based at least in part on (i) a subrange mapping scheme for a source-specific data type identifier code associated with the source-specific data type identifier field and (ii) the data value field for the inferred record;
generate an inferred codified field set comprising a plurality of inferred codified fields based at least in part on the one or more inferred records, wherein: (i) an inferred codified field of the plurality of inferred codified fields is associated with the inferred record and is generated based at least in part on the plurality of record fields for the inferred record, and (ii) the inferred codified field comprises an ingestion source identifier code that is generated based at least in part on the ingestion source identifier field for the inferred record, a source-specific data type identifier code associated with the source-specific data type identifier field for the respective inferred record, and the discretized data value code;
generate a temporally-arranged codified field set comprising a temporal arrangement of a group of input codified fields, wherein: (i) the group of input codified fields comprises the inferred codified field set and one or more input codified field sets, (ii) an input codified field of the one or more input codified field sets is associated with a corresponding temporal marker, and (iii) the corresponding temporal marker for the inferred codified field is generated based at least in part on the respective temporal marker for the non-codified input data object that is used to generate the inferred codified field;
generate, using a temporally encoded prediction machine learning model, a predictive output based at least in part on the temporally-arranged codified field set; and
perform one or more prediction-based actions based at least in part on the temporally-arranged codified field set.

10. The system of claim 9, wherein, given T temporal markers that are associated with a temporal marker sequence:
the temporally-arranged codified field set comprises a subset sequence of T codified field subsets;
a codified field subset of the temporally-arranged codified field set is associated with an associated temporal marker in the temporal marker sequence; and
the subset sequence is determined based at least in part on the temporal marker sequence.

11. The system of claim 9, wherein the one or more processors are further configured to:
identify a total value range associated with the source-specific data type identifier code that is associated with the inferred record for the inferred codified field;
determine S value subranges for the total value range, wherein Sis defined by a range segmentation count hyperparameter for the source-specific data type identifier code that is associated with the inferred record for the inferred codified field;
determine a selected value subrange from the S value subranges for the inferred codified field based at least in part on the data value field for the inferred record for the inferred codified field; and
generate the discretized data value code based at least in part on the selected value subrange.

12. The system of claim 11, wherein the subrange mapping scheme maps each value subrange in the S value subranges to a respective subrange coding symbol.

13. The system of claim 12, wherein the one or more processors are further configured to:
identify the respective subrange coding symbol for the selected value subrange based at least in part on the subrange mapping scheme; and
generate the discretized data value code based at least in part on the respective subrange coding symbol.

14. The system of claim 9, wherein the temporally encoded prediction machine learning model comprises a recurrent neural network machine learning model.

15. The system of claim 9, wherein the temporally encoded prediction machine learning model comprises an encoder machine learning model that is trained as part of an encoder-decoder machine learning architecture.

16. The system of claim 9, wherein the one or more processors are further configured to:
generate a natural language embedding vector for a natural language field associated with the inferred record; and
generate the data value field based at least in part on a vector distribution measure for the natural language embedding vector.

17. One or more non-transitory computer-readable storage media comprising instructions that, when executed by one or more processors, cause the one or more processors to:
identify a non-codified input data object that is generated by a respective data ingestion source of a plurality of data ingestion sources and is associated with a respective temporal marker of a plurality of temporal markers;
generate an inferred record set comprising one or more inferred records based at least in part on the non-codified input data object, wherein: (i) an inferred record of the inferred record set is associated with a record field set comprising a plurality of record fields, and (ii) the plurality of record fields for the inferred record comprises an ingestion source identifier field, a source-specific data type identifier field, and a data value field;

generate a discretized data value code for the inferred record based at least in part on (i) a subrange mapping scheme for a source-specific data type identifier code associated with the source-specific data type identifier field and (ii) the data value field for the inferred record;

generate an inferred codified field set comprising a plurality of inferred codified fields based at least in part on the one or more inferred records, wherein: (i) an inferred codified field of the plurality of inferred codified fields is associated with the inferred record and is generated based at least in part on the plurality of record fields for the inferred record, and (ii) the inferred codified field comprises an ingestion source identifier code that is generated based at least in part on the ingestion source identifier field for the inferred record, a source-specific data type identifier code associated with the source-specific data type identifier field for the inferred record, and the discretized data value code;

generate a temporally-arranged codified field set comprising a temporal arrangement of a group of input codified fields, wherein: (i) the group of input codified fields comprises the inferred codified field set and one or more input codified field sets, (ii) an input codified field of the one or more input codified field sets is associated with a corresponding temporal marker, and (iii) the corresponding temporal marker for the inferred codified field is generated based at least in part on the respective temporal marker for the non-codified input data object that is used to generate the inferred codified field;

generate, using a temporally encoded prediction machine learning model, a predictive output based at least in part on the temporally-arranged codified field set; and perform one or more prediction-based actions based at least in part on the temporally-arranged codified field set.

18. The one or more non-transitory computer-readable storage media of claim 17, wherein, given T temporal markers that are associated with a temporal marker sequence:

the temporally-arranged codified field set comprises a subset sequence of T codified field subsets;

a codified field subset of the temporally-arranged codified field set is associated with an associated temporal marker in the temporal marker sequence; and the subset sequence is determined based at least in part on the temporal marker sequence.

19. The one or more non-transitory computer-readable storage media of claim 17, wherein the instructions further cause the one or more processors to:

identify a total value range associated with the source-specific data type identifier code that is associated with the inferred record for the inferred codified field;

determine S value subranges for the total value range, wherein S is defined by a range segmentation count hyperparameter for the source-specific data type identifier code that is associated with the inferred record for the inferred codified field;

determine a selected value subrange from the S value subranges for the inferred codified field based at least in part on the data value field for the inferred record for the inferred codified field; and generate the discretized data value code based at least in part on the selected value subrange.

20. The one or more non-transitory computer-readable storage media of claim 19, wherein the subrange mapping scheme maps each value subrange in the S value subranges to a respective subrange coding symbol.

* * * * *